US012604661B2

(12) United States Patent
Jung et al.

(10) Patent No.: US 12,604,661 B2
(45) Date of Patent: Apr. 14, 2026

(54) LIGHT-EMITTING DEVICE INCLUDING FLUORESCENT COMPOUND, ELECTRONIC APPARATUS INCLUDING LIGHT-EMITTING DEVICE, AND FLUORESCENT COMPOUND

(71) Applicants: Samsung Electronics Co., Ltd., Suwon-si (KR); Ewha University—Industry Collaboration Foundation, Seoul (KR)

(72) Inventors: Yongsik Jung, Seoul (KR); Youngmin You, Seoul (KR); Juhyun Kim, Seoul (KR); Yusung Chun, Goyang-si (KR); Joonghyuk Kim, Seoul (KR); Dayoon Song, Daejeon (KR); Dongyeun Jeong, Seoul (KR); Seunghee Choi, Seoul (KR); Sooghang Ihn, Seoul (KR); Hyeonho Choi, Hwaseong-si (KR)

(73) Assignees: EWHA UNIVERSITY—INDUSTRY COLLABORATION FOUNDATION, Seoul (KR); SAMSUNG ELECTRONICS CO., LTD., Gyeonggi-Do (KR)

( * ) Notice: Subject to any disclaimer, the term of this patent is extended or adjusted under 35 U.S.C. 154(b) by 1083 days.

(21) Appl. No.: 17/682,249

(22) Filed: Feb. 28, 2022

(65) Prior Publication Data

US 2023/0078788 A1 Mar. 16, 2023

(30) Foreign Application Priority Data

Jul. 22, 2021 (KR) ........................ 10-2021-0096713

(51) Int. Cl.
*H10K 85/60* (2023.01)
*C07D 235/02* (2006.01)
(Continued)

(52) U.S. Cl.
CPC ....... *H10K 85/6572* (2023.02); *C07D 235/02* (2013.01); *C09K 11/06* (2013.01); *C09K 2211/1018* (2013.01); *H10K 50/11* (2023.02)

(58) Field of Classification Search
CPC ............. H10K 85/6572; H10K 85/623; C07D 235/02; C09K 11/06
See application file for complete search history.

(56) References Cited

U.S. PATENT DOCUMENTS

2004/0150327 A1* 8/2004 Kawai ................ H10K 85/6576 313/504
2008/0048571 A1* 2/2008 Yoon ...................... B82Y 20/00 315/169.3
(Continued)

FOREIGN PATENT DOCUMENTS

CN 105481794 A * 4/2016 ........... C07D 279/22
CN 108822088 A * 11/2018 ........... C07D 411/14
(Continued)

OTHER PUBLICATIONS

Baba, Masaaki, "Intersystem Crossing in the 1nπ* and 1ππ* States", Journal of Physical Chemistry, 2011, vol. 115, pp. 9514-9519, 6 pp.
(Continued)

*Primary Examiner* — Michael M Dollinger
(74) *Attorney, Agent, or Firm* — CANTOR COLBURN LLP

(57) ABSTRACT

A light-emitting device including an organic layer disposed between a first electrode and a second electrode, the organic layer comprising a fluorescent compound, wherein upon excitation, excitons in a $^3$n-π* excited state of the fluorescent compound migrate to a $^1$π-π* excited state of the fluorescent compound by reverse intersystem crossing with a Rate (rISC), and then undergo radiative transition to a ground state to emit light via fluorescence. The fluorescent compound is defined by a ratio of Rate (rISC) to Rate (IC) is 0.5
(Continued)

or greater. An electronic apparatus including the light-emitting device, and the fluorescent compound.

19 Claims, 1 Drawing Sheet

(51) Int. Cl.
*C09K 11/06* (2006.01)
*H10K 50/11* (2023.01)

(56) References Cited

U.S. PATENT DOCUMENTS

| | | | |
|---|---|---|---|
| 2018/0254425 A1 | 9/2018 | Lee et al. | |
| 2018/0294419 A1* | 10/2018 | Fuchiwaki | C07D 209/88 |
| 2019/0074445 A1 | 3/2019 | Ihn et al. | |
| 2020/0028094 A1 | 1/2020 | Sim et al. | |
| 2020/0083460 A1 | 3/2020 | Duan et al. | |
| 2021/0074933 A1* | 3/2021 | Yam | H05B 33/14 |
| 2022/0131086 A1* | 4/2022 | Lee | H10K 85/654 |
| 2022/0367828 A1 | 11/2022 | Kim et al. | |

FOREIGN PATENT DOCUMENTS

| | | |
|---|---|---|
| KR | 20180101952 A | 9/2018 |
| KR | 20190025503 A | 3/2019 |
| KR | 20200010004 A | 1/2020 |
| KR | 20200071313 A | 6/2020 |

OTHER PUBLICATIONS

Yi, Seung Yeon et al., “Blue Electrofluorescence Resulting from Exergonic Harvesting of Triplet Excitons”, Advanced Optical Materials, 2019, vol. 7, 1900630, 9 pp.

Zhao, Weijun et al., “Rational Molecular Design for Achieving Persistent and Efficient Pure Organic Room- Temperature Phosphorescence”, Chem, Cell Press, vol. 1, 2016, pp. 592-602, 12 pp.

English Translation of Office Action issued Apr. 21, 2025, in corresponding KR Patent Application No. 10-2021-0096713, 7 pp.

Office Action issued Apr. 21, 2025, in corresponding KR Patent Application No. 10-2021-0096713, 9 pp.

Yuwei Xu et al., “Fine Modulation of the Higher-Order Excitonic States toward More Efficient Conversion from Upper-Level Triplet to Singlet”, Journal of Physical Chemistry Letters, 2019, vol. 10, pp. 6878-6884.

* cited by examiner

LIGHT-EMITTING DEVICE INCLUDING FLUORESCENT COMPOUND, ELECTRONIC APPARATUS INCLUDING LIGHT-EMITTING DEVICE, AND FLUORESCENT COMPOUND

CROSS-REFERENCE TO RELATED APPLICATION

This application claims priority to Korean Patent Application No. 10-2021-0096713, filed on Jul. 22, 2021, in the Korean Intellectual Property Office, and all the benefits accruing therefrom under 35 U.S.C. § 119, the content of which is herein incorporated by reference in its entirety.

BACKGROUND

1. Field

The present disclosure relates to a light-emitting device including a fluorescent compound, an electronic apparatus including the light-emitting device, and the fluorescent compound.

2. Description of the Related Art

Among light-emitting devices, organic light-emitting devices (OLEDs) are self-emissive devices with relatively wide viewing angles, high contrast ratios, short response times, with desired brightness, driving voltage, and response speed characteristics, and thus, may provide a display with a full-color image.

OLEDs may include an anode, a cathode, and an organic layer that includes an emission layer disposed between the anode and the cathode. A hole transport region may be disposed between the anode and the emission layer, and an electron transport region may be disposed between the emission layer and the cathode. Holes provided from the anode move toward the emission layer through the hole transport region, and electrons provided from the cathode move toward the emission layer through the electron transport region. Carriers, such as holes and electrons, recombine in the emission layer to produce excitons. The excitons then transition from an excited state to a ground state resulting in light emission.

Examples of emission using triplet excitons include phosphorescence and thermally activated delayed fluorescence (TADF). Because the phosphorescence and the TADF may have a relatively long exciton lifetime, compound deterioration may occur rapidly, and consequently, device lifetime may by relatively shorter or decrease. In addition, the phosphorescent compounds used presently in OLEDs are metal complexes including iridium or platinum, each of which are very costly metals that may increase production and/or consumer costs for the device.

Therefore, unlike phosphorescent compounds and TADF compounds, there is a present need to develop fluorescent compounds with a unique emission mechanism to provide improved device performance characteristics. The fluorescent compound does not contain an expensive transition metal such as iridium or platinum and may substantially prevent device deterioration and have high luminance and high luminescence efficiency. In particular, there is a present need to develop fluorescent compounds with a unique emission that emit blue or deep-blue light.

SUMMARY

Provided is a light-emitting device that includes a fluorescent compound that may satisfy a certain electronic state condition, an electronic apparatus including the light-emitting device, and the fluorescent compound. Additional aspects will be set forth in part in the description which follows and, in part, will be apparent from the description, or may be learned by practice of the presented embodiments of the disclosure.

According to an aspect of an embodiment, an organic light-emitting device may include:

a first electrode, a second electrode facing the first electrode; and an organic layer disposed between the first electrode and the second electrode, the organic layer including an emission layer and a fluorescent compound, wherein, upon excitation, excitons in a $^3$n-π* excited state of the fluorescent compound may migrate to a $^1$π-π* excited state of the fluorescent compound by reverse intersystem crossing (rISC) having a Rate (rISC), and the excitons in the $^1$π-π* excited state undergo radiative transition to a ground state to emit light via fluorescence, and excitons in the $^3$n-π* excited state of the fluorescent compound may migrate to a $^3$π-π* excited state of the fluorescent compound through reverse internal conversion (IC) having a Rate (IC), wherein a ratio of Rate (rISC) to Rate (IC) may be 0.5 or greater, wherein the indice "$^3$" in "$^3$n-π*" and "$^3$π-π*" represents a triplet state, and the indice "$^1$" in "$^1$π-π*" represents a singlet state, Rate (rISC) may be evaluated by Equation 1, and Rate (IC) may be evaluated by Equation 2:

$$\text{Rate }(rISC)=SOC^2/(E(^3n\text{-}\pi^*)-E(^1\pi\text{-}\pi^*))^2 \quad \text{Equation 1}$$

$$\text{Rate }(IC)=SOC^2/(E(^3n\text{-}\pi^*)-E(^3\pi\text{-}\pi^*))^2 \quad \text{Equation 2}$$

wherein, in Equations 1 and 2,

SOC represents a spin-orbit coupling value,

E($^3$n-π*) represents an energy level of the $^3$n-π* excited state,

E($^1$π-π*) represents an energy level of the $^1$π-π* excited state,

E($^3$π-π*) represents an energy level of the $^3$π-π* excited state, and SOC, E($^3$n-π*), E($^1$π-π*), and E($^3$π-π*) may each be evaluated according to density functional theory (DFT).

According to an aspect of another embodiment, an electronic apparatus may include the light-emitting device.

According to an aspect of another embodiment, a fluorescent compound has at least one carbonyl group, wherein upon excitation, excitons in a $^3$n-π* excited state of the fluorescent compound may migrate to a $^1$π-π* excited state of the fluorescent compound through reverse intersystem crossing (rISC) having a Rate (rISC), and the excitons in the $^1$π-π* excited state undergo radiative transition to a ground state to emit light via fluorescence, and excitons in the $^3$n-π* excited state of the fluorescent compound may migrate to a $^3$π-π* excited state of the fluorescent compound through reverse internal conversion (IC) having a Rate (IC), a ratio of Rate (rISC) to Rate (IC) may be 0.5 or greater, the indice "$^3$" in "$^3$n-π*" and "$^3$π-π*" represents a triplet state, the indice "$^1$" in "$^1$π-π*" represents a singlet state, Rate (rISC) may be evaluated by Equation 1, and Rate (IC) may be evaluated by Equation 2.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
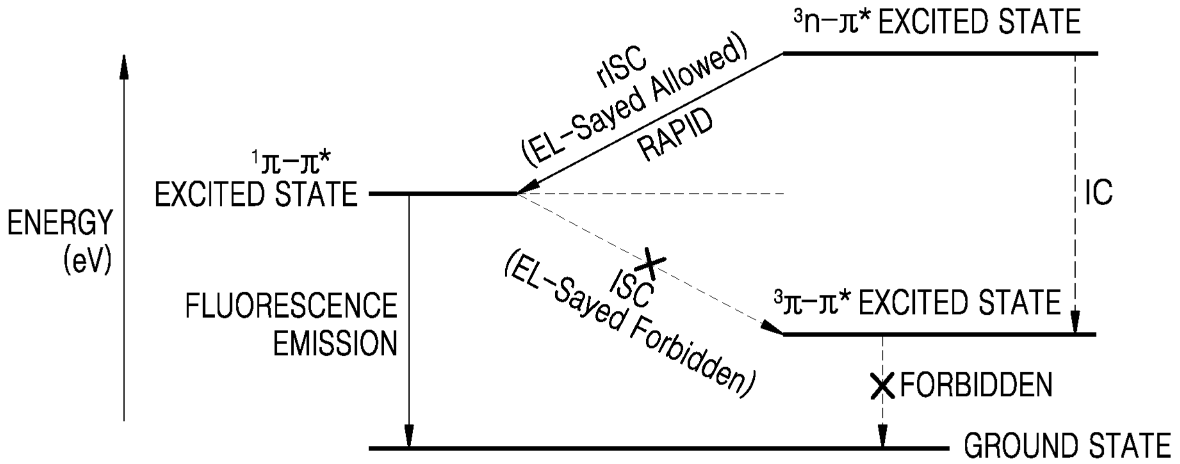
FIG. 1 is a schematic representation of an emission mechanism of a fluorescent compound according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects.

It will be understood that when an element is referred to as being "on" another element, it can be directly on the other element or intervening elements may be present therebetween. In contrast, when an element is referred to as being "directly on" another element, there are no intervening elements present.

It will be understood that, although the terms "first," "second," "third," etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section.

The terminology used herein is for the purpose of describing particular embodiments only and is not intended to be limiting. As used herein, the singular forms "a," "an," and "the" are intended to include the plural forms, including "at least one," unless the content clearly indicates otherwise. "At least one" is not to be construed as limiting "a" or "an." "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

FIG. 1 illustrates an emission mechanism of a fluorescent compound according to an embodiment included in a light-emitting device. Referring to FIG. 1, the fluorescent compound will be described in detail. The fluorescent compound may have $^{3}n\text{-}\pi^{*}\text{-to-}^{1}\pi\text{-}\pi^{*}$ transition. That is, the fluorescent compound may have a $^{3}n\text{-}\pi^{*}$ excited state and may be identified to have $^{3}n\text{-}\pi^{*}\text{-to-}^{1}\pi\pi^{*}$ transition. The $^{3}n\text{-}\pi^{*}\text{-to-}^{1}\pi\text{-}\pi^{*}$ transition of the fluorescent compound may be identified by using an infrared (IR) transient absorption spectrometer.

As shown in FIG. 1, excitons of the $^{3}n\text{-}\pi^{*}$ excited state in the fluorescent compound may migrate to the $^{1}\pi\text{-}\pi^{*}$ excited state of the fluorescent compound by reverse intersystem crossing (rISC) with a Rate (rISC), and excitons of $^{3}n\text{-}\pi^{*}$ excited state in the fluorescent compound may migrate to the $^{3}\pi\text{-}\pi^{*}$ excited state of the fluorescent compound by internal conversion (IC) with a Rate (IC). Accordingly, a rISC rate at which excitons of the $^{3}n\text{-}\pi^{*}$ excited state in the fluorescent compound migrate to the $^{1}\pi\text{-}\pi^{*}$ excited state in the fluorescent compound is defined as Rate (rISC), and an IC rate at which excitons in the $^{3}n\text{-}\pi^{*}$ excited state of the fluorescent compound migrate to the $^{3}\pi\text{-}\pi^{*}$ excited state of the fluorescent compound is defined as Rate (IC). The indice "$^{3}$" in "$^{3}n\text{-}\pi^{*}$" and "$^{3}\pi\text{-}\pi^{*}$" represents a triplet state, and the indice"$^{1}$" in "$^{1}\pi\text{-}\pi^{*}$" represents a singlet state.

Excitons in the $^{1}\pi\text{-}\pi^{*}$ excited state of the fluorescent compound may undergo radiative transition to a ground state resulting in light emission via fluorescence.

In some embodiments, excitons that migrate from the $^{3}n\text{-}\pi^{*}$ excited state to the $^{1}\pi\text{-}\pi^{*}$ excited state of the fluorescent compound by rISC may undergo radiative transition to a ground state resulting in light emission via fluorescence. In some instances, excitons of the $^{1}\pi\text{-}\pi^{*}$ excited state will migrate via intersystem crossing (ISC) to the $^{3}\pi\text{-}\pi^{*}$ excited state in the fluorescent compound, however, such a migration is highly disfavored or spin forbidden. Moreover, the radiative transition of excitons of the $^{3}n\text{-}\pi^{*}$ excited state in the fluorescent compound to the ground state is also disfavored, and therefore excitons of the $^{3}\pi\text{-}\pi^{*}$ excited state in the fluorescent compound may not substantially undergo transition to the ground state. That is, excitons of the $^{3}\pi\text{-}\pi^{*}$ excited state in the fluorescent compound may not substantially contribute to emission.

A ratio of Rate (rISC) to Rate (IC) may be 0.5 or greater, 0.8 or greater, or 1.0 or greater. In some embodiments, a ratio of Rate (rISC) to Rate (IC) may be in a range of about 0.5 to about 9.0, about 0.8 to about 9.0, about 0.8 to about 1.5, or about 1.0 to about 1.3. A ratio of Rate (rISC) to Rate (IC) may be calculated as Rate (rISC)/Rate (IC).

As the ratio of Rate (rISC) to Rate (IC) is within any of the above ranges, many if not most of excitons of the $^{3}n\text{-}\pi^{*}$ excited state may migrate to the $^{1}\pi\text{-}\pi^{*}$ excited state in the fluorescent compound, and then undergo radiative transition to the ground state. Thus, in theory, the fluorescent compound may exhibit excellent luminescence efficiency, e.g., close to 100 percent (%), such as greater than 80% or 90%. In addition, the fluorescent compound having the ratio of Rate (rISC) to Rate (IC) within any of the above ranges may have a short exciton lifetime, i.e., a short decay time. Accordingly, when driving a light-emitting device including the fluorescent compound, the likelihood that such a high energy state would lead to deterioration of the fluorescent compound may be reduced, and therefore, the light-emitting device may exhibit improved lifespan characteristics or performance.

In addition, the fluorescent compound as described may not contain an expensive transition metal such as iridium or platinum, and still provide a high luminescence efficiency and greater lifespan. Accordingly, when a fluorescent compound is used as described in a light-emitting device, the device may exhibit relatively high luminescence efficiency and greater lifespan performance, and may be manufactured at a relatively low cost.

In an embodiment, the Rate (rISC) may be in a range of about $7.8\times10^{-9}$ atomic units (au) to about $3.3\times10^{-7}$ au.

In one or more embodiments, Rate (IC) may be in a range of about $3.8\times10^{-9}$ au to about $2.5\times10^{-7}$ au.

In one or more embodiments, an energy level of the $^3$n-π* excited state may be greater than the lowest energy level among energy levels of the $^1$π-π* excited state in the fluorescent compound.

In one or more embodiments, an absolute value of a difference between an energy level of the $^3$n-π* excited state in the fluorescent compound and the lowest energy level among energy levels of the $^1$π-π* excited state in the fluorescent compound may be in a range of 0 electron volts (eV) to about 0.15 eV, about 0.02 eV to about 0.10 eV, or about 0.04 eV to about 0.08 eV.

In one or more embodiments, an energy level of the $^3$n-π* excited state may be greater than an energy level of the $^3$π-π* excited state in the fluorescent compound.

In one or more embodiments, an absolute value of a difference between an energy level of the $^3$n-π* excited state in the fluorescent compound and an energy level of the $^3$π-π* excited state in the fluorescent compound may be in a range of about 0 eV to about 0.10 eV, about 0.02 eV to about 0.08 eV, or about 0.04 eV to about 0.06 eV.

In one or more embodiments, an additional excited state may not be present between the $^3$n-π* excited state and the $^3$π-π* excited state in the fluorescent compound.

In the present specification and claims, the indice "$^3$" in "$^3$n-π*" and "$^3$π-π*" represents a triplet state, and the indice "$^1$" in "$^1$π-π*" represents a singlet state. "$^3$n-π*" and "$^3$π-π*" may respectively be represented by "triplet n-π*" and "triplet π-π*", and "$^1$π-π*" may be represented by "singlet π-π*".

In the present specification, an energy level of $^1$π-π* excited state, an energy level of $^3$n-π* excited state, and an energy level of $^3$π-π* excited state may each be evaluated according to density functional theory (DFT). For example, the energy level of $^1$π-π* excited state, the energy level of $^3$n-π* excited state, and the energy level of $^3$π-π*excited state may each be evaluated according to time dependent-density functional theory (TD-DFT) method, for example, by using program Gaussian 09, wherein structure optimization is performed at a degree of CAM-B3LYP/6-311+G(d, p).

Rate (rISC) and Rate (IC) may each be evaluated according to quantum chemistry computation. For example, Rate (rISC) may be evaluated according to Equation 1, and Rate (IC) may be evaluated according to Equation 2:

$$\text{Rate }(rISC)=SOC^2/(E(^3n\text{-}\pi^*)-E(^1\pi\text{-}\pi^*))^2 \quad \text{Equation 1}$$

$$\text{Rate }(IC)=SOC^2/(E(^3n\text{-}\pi^*)-E(^3\pi\text{-}\pi^*))^2 \quad \text{Equation 2}$$

wherein, in Equations 1 and 2,

SOC represents a spin-orbit coupling value,

E($^3$n-π*) represents an energy level of the $^3$n-π* excited state,

E($^1$π-π*) represents an energy level of the $^1$π-π* excited state,

E($^3$π-π*) represents an energy level of the $^3$π-π* excited state, and

SOC, E($^3$n-π*), E($^1$π-π*), and E($^3$π-π*) may each be evaluated according to density functional theory (DFT).

In an embodiment, the evaluation method of Rate (rISC) and Rate (IC) may be understood according to Evaluation Example 2.

The fluorescent compound may have a non-bonding orbital (e.g., a non-bonding π orbital) that may induce $^3$n-π*-to-$^1$π-π* transition as described above. For example, the fluorescent compound may have at least one carbonyl group.

In an embodiment, the fluorescent compound may be represented by Formula 1-1:

Formula 1-1

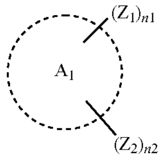

Formula 2-1

$$*-(L_1)_{a1}-(R_1)_{b1}$$

Formula 2-2

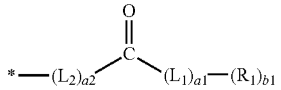

wherein, in Formula 1-1, ring $A_1$ may be a $C_5$-$C_{60}$ carbocyclic group or a $C_1$-$C_{60}$ heterocyclic group, $Z_1$ in Formula 1-1 may be a group represented by Formula 2-1 or a group represented by Formula 2-2, and n1 may be an integer from 0 to 20, $Z_2$ in Formula 1-1 may be a group represented by Formula 2-2, and n2 may be an integer from 1 to 40, $L_1$ and $L_2$ in Formulae 2-1 and 2-2 may each independently be a single bond, a $C_5$-$C_{60}$ carbocyclic group unsubstituted or substituted with at least one $R_{10a}$, or a $C_1$-$C_{60}$ heterocyclic group unsubstituted or substituted with at least one $R_{10a}$, a1 and a2 in Formulae 2-1 and 2-2 may each independently be an integer from 1 to 20, wherein $R_1$ and each $R_{10a}$ in Formulae 2-1 and 2-2 may be each independently hydrogen, deuterium, —F, —Cl, —Br, —I, —$SF_5$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$, —$B(Q_6)(Q_7)$, or —$P(=O)(Q_8)(Q_9)$, b1 in Formulae 2-1 and 2-2 may be an integer from 1 to 20,

* in Formulae 2-1 and 2-2 indicates a binding site to an adjacent atom, and at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, —$B(Q_{16})(Q_{17})$, —$P(=O)(Q_{18})(Q_{19})$, or any combination thereof;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a Cl—CH alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, —$B(Q_{26})(Q_{27})$, —$P(=O)(Q_{28})(Q_{29})$, or any combination thereof; or —$N(Q_{31})(Q_{32})$, —$Si(Q_{33})(Q_{34})(Q_{35})$, —$B(Q_{36})(Q_{37})$, or —$P(=O)(Q_{38})(Q_{39})$, wherein $Q_1$ to $Q_9$, $Q_{11}$ to $Q_{19}$, $Q_{21}$ to $Q_{29}$, and $Q_{31}$ to $Q_{39}$ may each independently be hydrogen, deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one selected from deuterium; a $C_1$-$C_{60}$ alkyl group; and a $C_6$-$C_{60}$ aryl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one selected from deuterium; a $C_1$-$C_{60}$ alkyl group; and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group.

For example, ring $A_1$ in Formula 1-1 may be a nitrogen-containing $C_5$-$C_{60}$ heteropolycyclic group.

In some embodiments, ring $A_1$ in Formula 1-1 may be a $C_{18}$-$C_{60}$ carbocyclic group in which at least four rings are condensed (e.g., a chrysene group, a triphenylene group, or a perylene group).

In an embodiment, ring $A_1$ in Formula 1-1 may be a group represented by one of Formulae A1-1 to A1-6:

A1-1

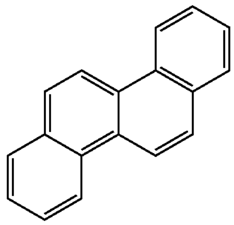

A1-2

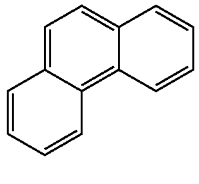

A1-3

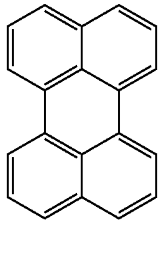

-continued

A1-4

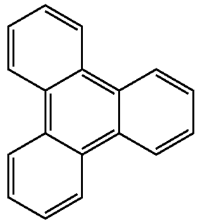

A1-5

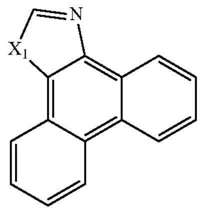

A1-6

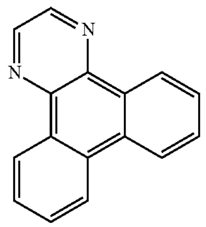

wherein, in Formula A1-5, $X_1$ may be O, S, N($Z_1$), N($Z_2$), or C($Z_{11}$)($Z_{12}$),wherein $Z_{11}$ and $Z_{12}$ are defined above, and may each be understood by referring to the description of $Z_1$ provided herein.

In Formula 1-1, n1 and n2 may respectively indicate the number of $Z_1$(s) and $Z_2$(s) groups to ring $A_1$. When n1 is 2 or greater, at least two $Z_1$(s) may be identical to or different from each other, and when n2 is 2 or greater, at least two $Z_2$(s) may be identical to or different from each other. For example, n1 may be 0, 1, or 2. In some embodiments, n2 may be 1 or 2.

In one or more embodiments, in Formulae 2-1 and 2-2, $L_1$ and $L_2$ may each independently be a benzene group, a pentalene group, an indene group, a naphthalene group, an azulene group, a heptalene group, an indacene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, a hexacene group, a rubicene group, a coronene group, an ovalene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, an isoindole group, an indole group, an indazole group, a quinoline group, an isoquinoline group, a benzoquinoline group, a phthalazine group, a naphthyridine group, a quinoxaline group, a quinazoline group, a cinnoline group, a carbazole group, a phenanthridine group, an acridine group, a phenanthroline group, a phenazine group, a benzimidazole group, a benzofuran group, a benzothiophene group, a benzothiazole group, a benzoxazole group, a triazole group, a dibenzofuran group, a dibenzothiophene group, a triazine group, a benzocarbazole group, a dibenzocarbazole group, or an imidazopyridine group, each unsubstituted or substituted with deuterium, —F, —Cl, —Br, —I, $—CD_3$, $—CD_2H$, $—CDH_2$, $—CF_3$, $—CF_2H$, $—CFH_2$, a hydroxyl group, a cyano group, a nitro group, an amino group, an am idino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, an imidazopyrimidinyl group, —Si($Q_{33}$)($Q_{34}$)($Q_{35}$), or any combination thereof. $Q_{33}$ to $Q_{35}$ may respectively be understood by referring to the descriptions of $Q_1$ to $Q_9$ provided herein.

In one or more embodiments, in Formula 1-1, $L_1$ and $L_2$ may each independently be

- a single bond; or
- a benzene group, a naphthalene group, a phenanthrene group, a chrysene group, a triphenylene group, a pyridine group, a pyrimidine group, or a triazine group, each of which is unsubstituted or substituted with deuterium, a $C_1$-$C_{20}$ alkyl group, a phenyl group, a biphenyl group, or any combination thereof.

In Formula 1-1, a1 and a2 may respectively indicate the number of $L_1$(s) and $L_2$(s). When a1 is 2 or greater, at least two $L_1$(s) may be identical to or different from each other, and when a2 is 2 or greater, at least two $L_2$(s) may be identical to or different from each other. For example, a1 and a2 may each independently be 1, 2, or 3.

In an embodiment, $R_1$ in Formulae 2-1 and 2-2 may be:

- hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, or a $C_1$-$C_{20}$ alkoxy group;
- a $C_1$-$C_{20}$ alkyl group or a $C_1$-$C_{20}$ alkoxy group, each substituted with deuterium, —F, —Cl, —Br, —I, $—CD_3$, $—CD_2H$, $—CDH_2$, $—CF_3$, $—CF_2H$, $—CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, or any combination thereof;

a cyclopentyl group, a cydohexyl group, a cydoheptyl group, a cydooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, or an imidazopyrimidinyl group, each unsubstituted or substituted with deuterium, —F, —Cl, —Br, —I, $—CD_3$, $—CD_2H$, $—CDH_2$, $—CF_3$, $—CF_2H$, $—CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cydohexyl group, a cydoheptyl group, a cydooctyl group, an adamantanyl group, a norbornanyl group, a norbornenyl group, a cyclopentenyl group, a cyclohexenyl group, a cycloheptenyl group, a phenyl group, a biphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, an imidazopyrimidinyl group, $—Si(Q_{33})(Q_{34})(Q_{35})$, or any combination thereof; or $—N(Q_1)(Q_2)$, $—Si(Q_3)(Q_4)(Q_5)$, $—B(Q_6)(Q_7)$, or $—P(=O)(Q_8)(Q_9)$, wherein $Q_1$ to $Q_9$ and $Q_{33}$ to $Q_{35}$ may each independently be:

$—CH_3$, $—CD_3$, $—CD_2H$, $—CDH_2$, $—CH_2CH_3$, $—CH_2CD_3$, $—CH_2CD_2H$, $—CH_2CDH_2$, $—CHDCH_3$, $—CHDCD_2H$, $—CHDCDH_2$, $—CHDCD_3$, $—CD_2CD_3$, $—CD_2CD_2H$, and $—CD_2CDH_2$; or an n-propyl group, an iso-propyl group, an n-butyl group, an isobutyl group, a sec-butyl group, a tert-butyl group, an n-pentyl group, an isopentyl group, a sec-pentyl group, a tert-pentyl group, a phenyl group, or a naphthyl group, each unsubstituted or substituted with deuterium, a $C_1$-$C_{10}$ alkyl group, a phenyl group, or any combination thereof.

In an embodiment, in Formulae 2-1 and 2-2, $R_1$ may be hydrogen, deuterium, a $C_1$-$C_{20}$ alkyl group, a phenyl group, or a biphenyl group.

In one or more embodiments, the fluorescent compound may be a compound represented by Formula A(1) or Formula A(2):

A(1)

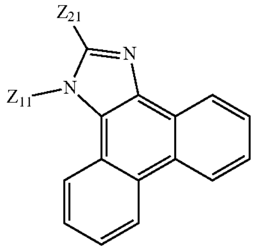

A(2)

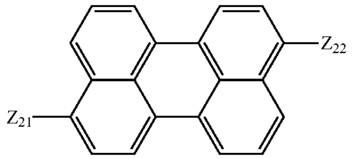

wherein, in Formulae A(1) and A(2), $Z_{11}$ and $Z_{12}$ may each be understood by referring to the description of $Z_1$ provided herein, and $Z_{21}$ and $Z_{22}$ may each be understood by referring to the description of $Z_2$ provided herein.

In one or more embodiments, the fluorescent compound may be one of Compounds 1, 2, 3, or 4:

1

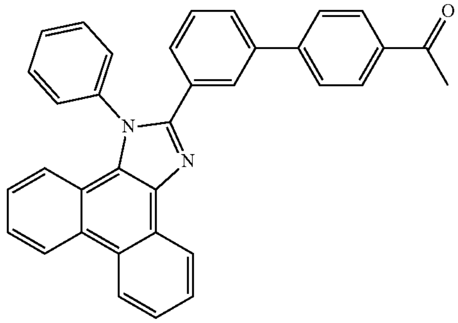

-continued

2

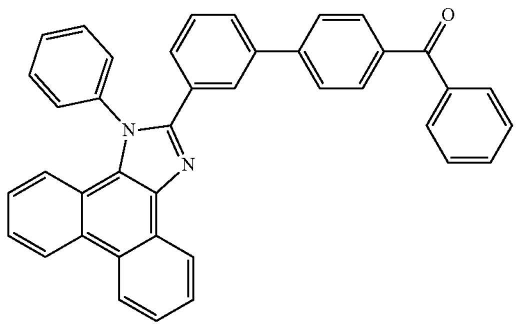

3

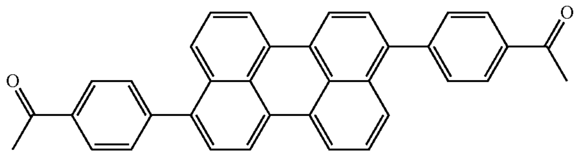

4

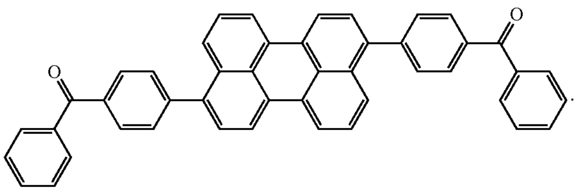

The fluorescent compound may be included in an emission layer of the light-emitting device.

The fluorescent compound included in the emission layer may emit light via fluorescence according to an emission mechanism shown in FIG. 1.

The emission layer may further include, in addition to the fluorescent compound, any suitable host. The host may consist of one type of compound or a mixture of two different types of compounds. When the emission layer further includes a host, the fluorescent compound in the emission layer may serve as a fluorescence emitter, and a content of the fluorescent compound may be smaller than a content of the host.

For example, the host may include a fluorene-containing compound, a carbazole-containing compound, a dibenzofuran-containing compound, a dibenzothiophene-containing compound, an indenocarbazole-containing compound, an indolocarbazole-containing compound, a benzofurocarbazole-containing compound, a benzothienocarbazole-containing compound, an acridine-containing compound, a dihydroacridine-containing compound, a triindolobenzene-containing compound, a pyridine-containing compound, a pyrimidine-containing compound, a triazine-containing compound, a silicon-containing compound, a cyano-containing compound, a phosphineoxide-containing compound, a sulfoxide-containing compound, a sulfonyl-containing compound, or any combination thereof.

For example, the host may include a compound including at least one carbazole ring and at least one cyano group or a phosphine oxide-containing compound.

The host may include, for example, at least one of CBP, mCBP(Compound H7), and one of Compounds H1 to H6 or H8 to H24:

H1

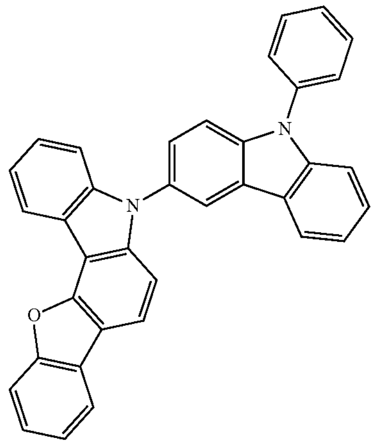

H2

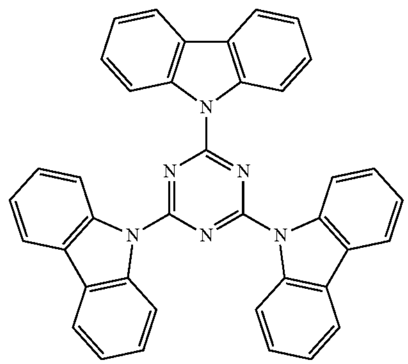

H3

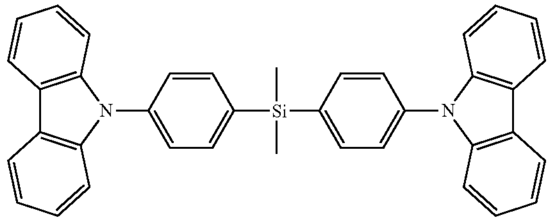

H4

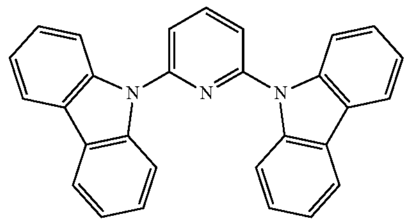

-continued
H5
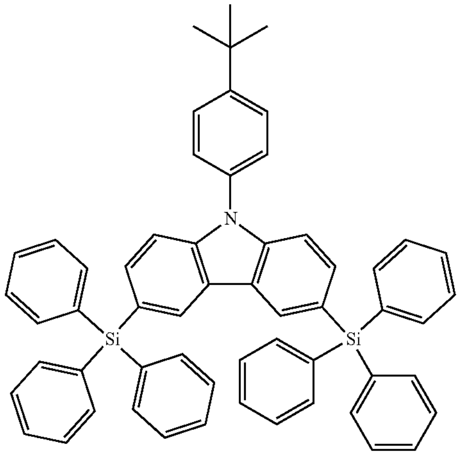
H6
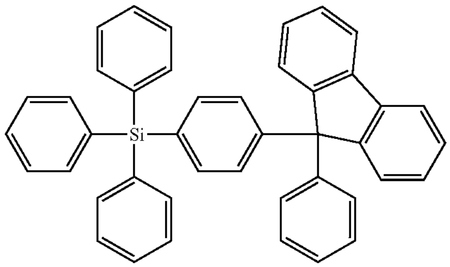
H7
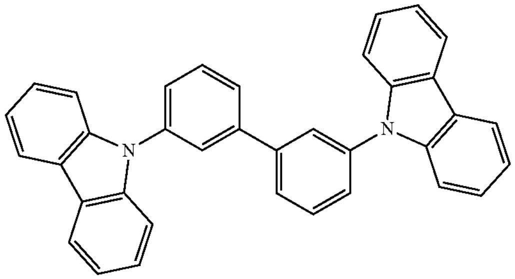
H8
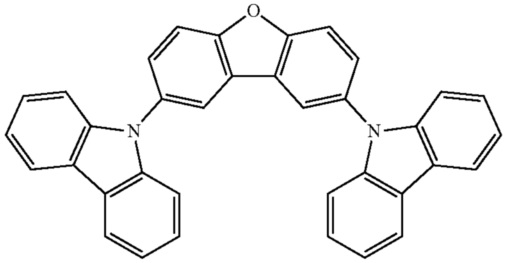
H9
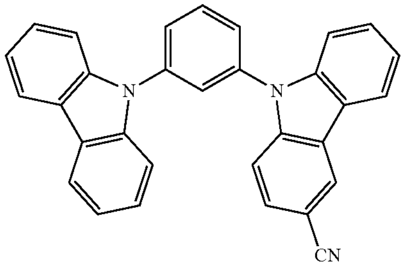
-continued
H10
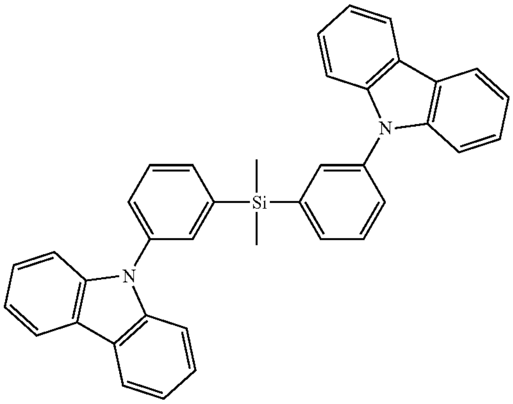
H11
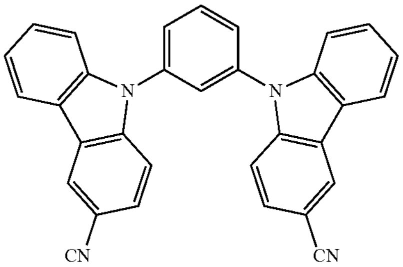
H12
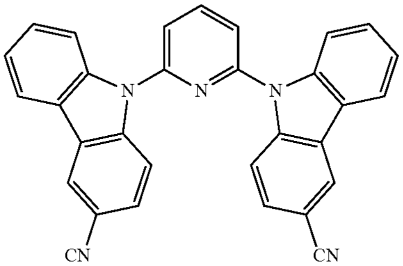
H13
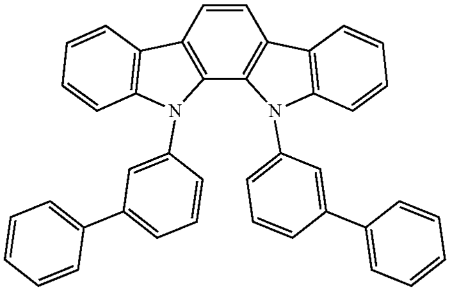
H14
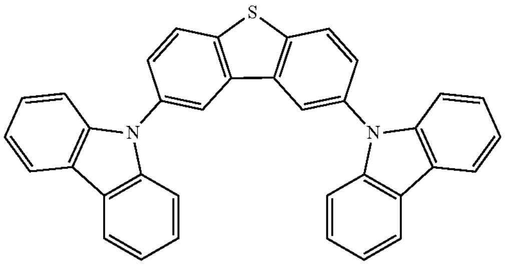

-continued
H15
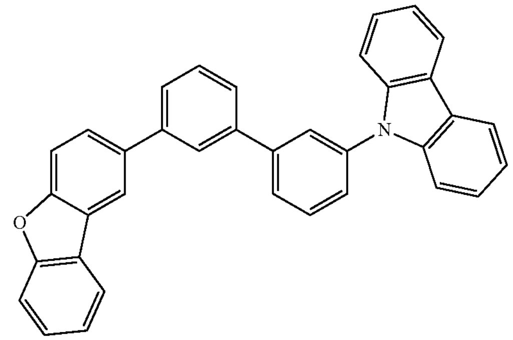
H16
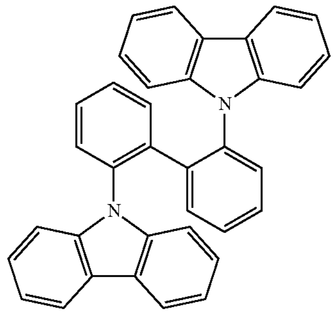
H17
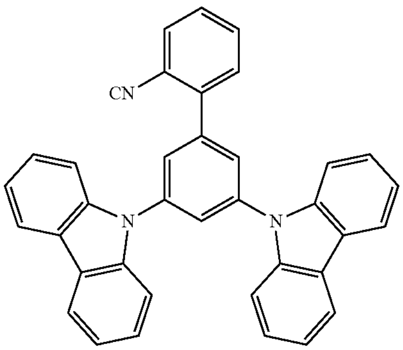
H18
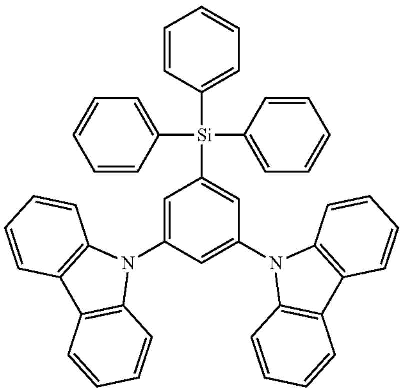
-continued
H19
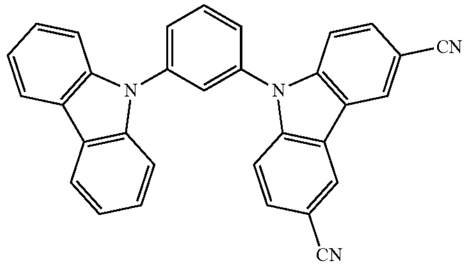
H20
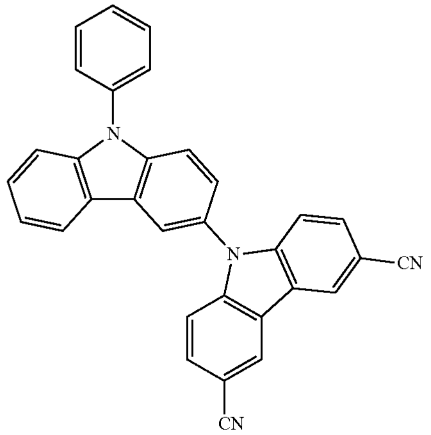
H21
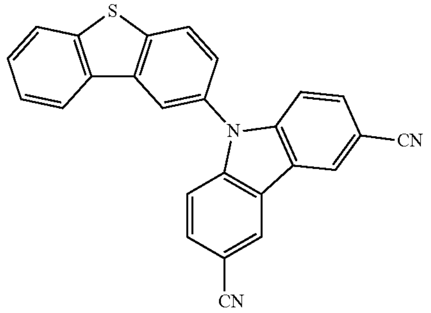
H22
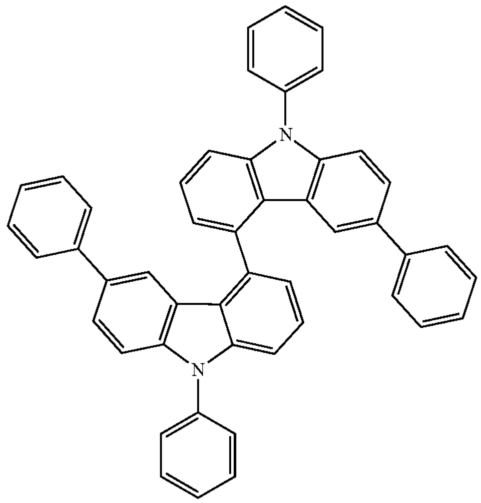

-continued

H23

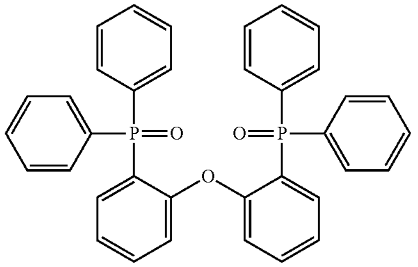

H24

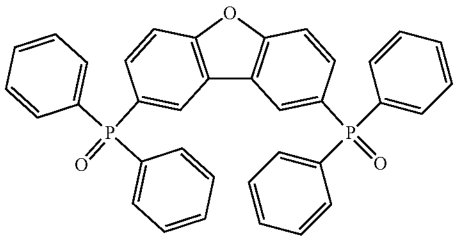

For example, the organic layer may further include a hole transport region disposed between the first electrode and the emission layer and an electron transport region disposed between the emission layer and the second electrode, wherein the hole transport region may include a hole injection layer, a hole transport layer, an electron blocking layer, a buffer layer, or a combination thereof, and the electron transport region may include a hole blocking layer, an electron transport layer, an electron injection layer, or a combination thereof.

Figure 2:
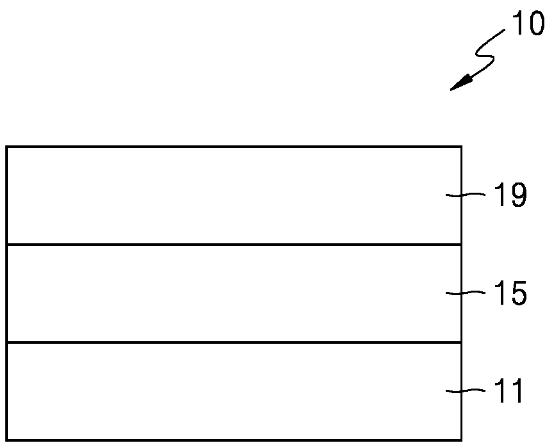
FIG. 2 is a schematic cross-sectional representation of a light-emitting device according to an embodiment.

FIG. 2 is a schematic view of an embodiment of a light-emitting device, an organic light-emitting device 10. Hereinafter, a structure and a method of manufacturing the organic light-emitting device according to an embodiment will be described with reference to FIG. 2. The organic light-emitting device 10 may include a first electrode 11, an organic layer 15, and a second electrode 19.

A substrate may be additionally disposed under the first electrode 11 or on the second electrode 19. The substrate may be a conventional substrate used in organic light-emitting devices, e.g., a glass substrate or a transparent plastic substrate, each having excellent mechanical strength, thermal stability, transparency, surface smoothness, ease of handling, and water repellency.

The first electrode 11 may be produced by depositing or sputtering, onto the substrate, a material for forming the first electrode 11. The first electrode 11 may be an anode. The material for forming the first electrode 11 may include a material with a high work function for easy hole injection. The first electrode 11 may be a reflective electrode, a semi-transmissive electrode, or a transmissive electrode. The material for forming the first electrode 11 may be indium tin oxide (ITO), indium zinc oxide (IZO), tin oxide ($SnO_2$), or zinc oxide (ZnO). In some embodiments, the material for forming the first electrode 11 may be a metal, such as magnesium (Mg), aluminum (Al), silver (Ag), aluminum-lithium (Al—Li), calcium (Ca), magnesium-indium (Mg—In), or magnesium-silver (Mg—Ag).

The first electrode 11 may have a single-layered structure or a multi-layered structure including a plurality of layers. In some embodiments, the first electrode 11 may have a triple-layered structure of ITO/Ag/ITO.

The organic layer 15 may be on the first electrode 11.

The organic layer 15 may include a hole transport region, an emission layer, and an electron transport region.

The hole transport region may be between the first electrode 11 and the emission layer.

The hole transport region may include a hole injection layer, a hole transport layer, an electron blocking layer, a buffer layer, or a combination thereof.

The hole transport region may include a hole injection layer only or a hole transport layer only. In some embodiments, the hole transport region may include a hole injection layer and a hole transport layer which are sequentially stacked on the first electrode 11. In some embodiments, the hole transport region may include a hole injection layer, a hole transport layer, and an electron blocking layer, which are sequentially stacked on the first electrode 11.

When the hole transport region includes a hole injection layer, the hole injection layer may be formed on the first electrode 11 by using one or more suitable methods, such as vacuum deposition, spin coating, casting, and Langmuir-Blodgett (LB) deposition.

When a hole injection layer is formed by vacuum-deposition, for example, the vacuum deposition may be performed at a temperature in a range of about 100° C. to about 500° C., at a vacuum degree in a range of about $10^{-8}$ torr to about $10^{-3}$ torr, and at a rate in a range of about 0.01 Angstroms per second (Å/sec) to about 100 Å/sec, though the conditions may vary depending on a compound used as a hole injection material and a structure and thermal properties of a desired hole injection layer.

When a hole injection layer is formed by spin coating, the spin coating may be performed at a coating rate in a range of about 2,000 revolutions per minute (rpm) to about 5,000 rpm, and at a temperature in a range of about 80° C. to 200° C., to facilitate removal of a solvent after the spin coating, though the conditions may vary depending on a compound that is used as a hole injection material and a structure and thermal properties of a desired hole injection layer.

The conditions for forming a hole transport layer and an electron blocking layer may be inferred from the conditions for forming the hole injection layer.

The hole transport region may include m-MTDATA, TDATA, 2-TNATA, NPB, β-NPB, TPD, spiro-TPD, spiro-NPB, methylated-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate)(PEDOT/PSS), polyaniline/camphor-sulfonic acid (PANI/CSA), polyaniline/poly(4-styrene sulfonate) (PANI/PSS), a compound represented by Formula 201, a compound represented by Formula 202, or any combination thereof:

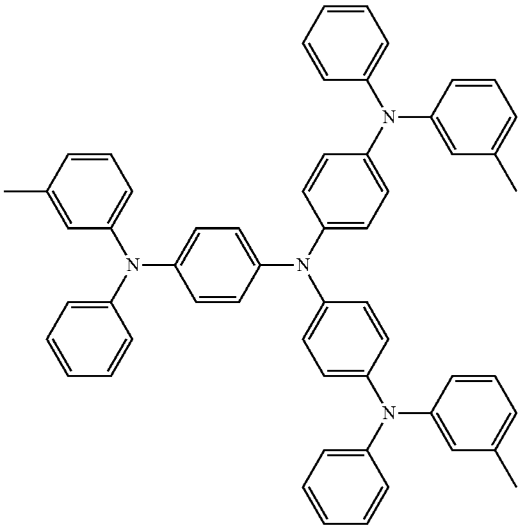
m-MTDATA
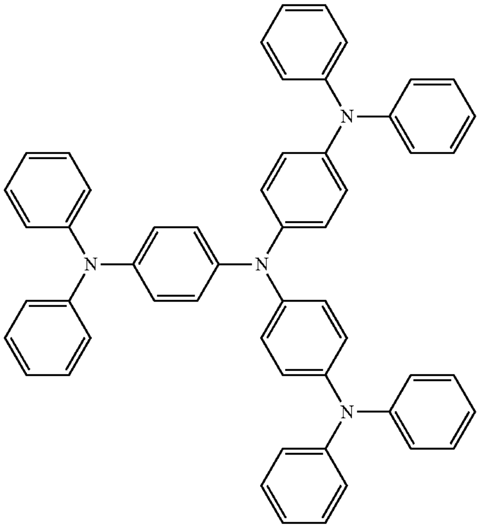
TDATA
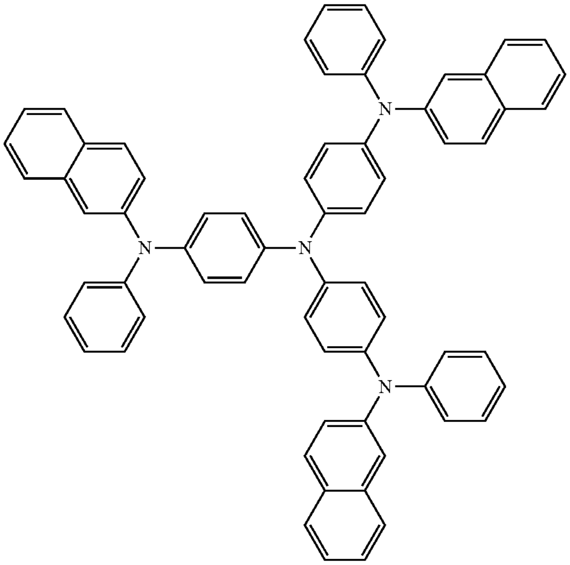
2-TNATA
-continued
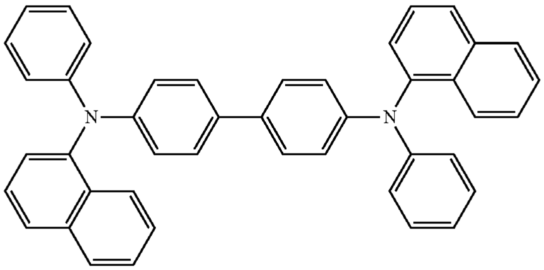
NPB
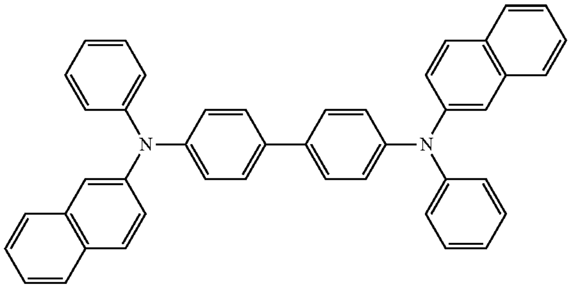
β-NPB
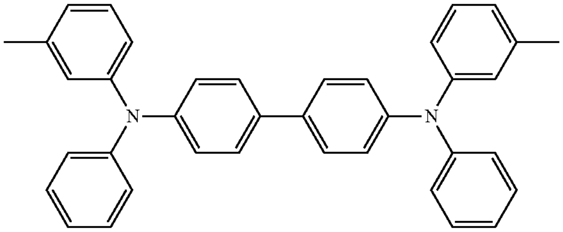
TPD
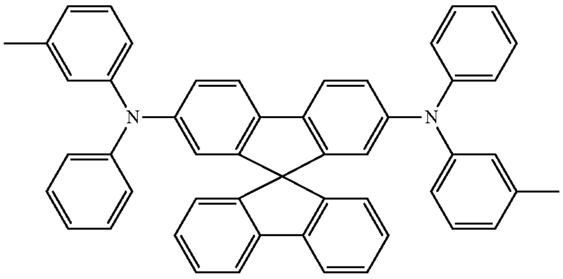
Spiro-TPD
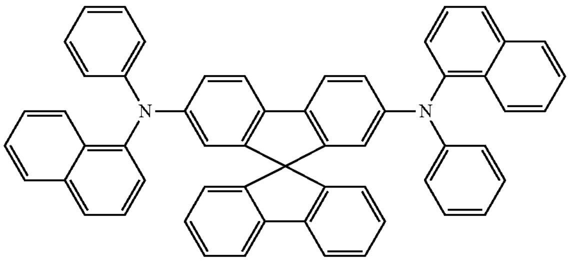
Spiro-NPB -continued

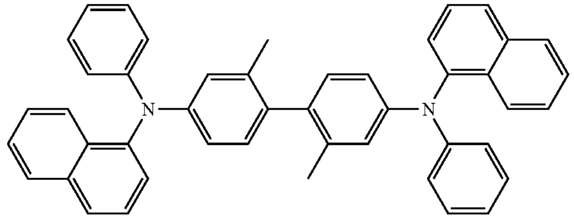

methylated NPB

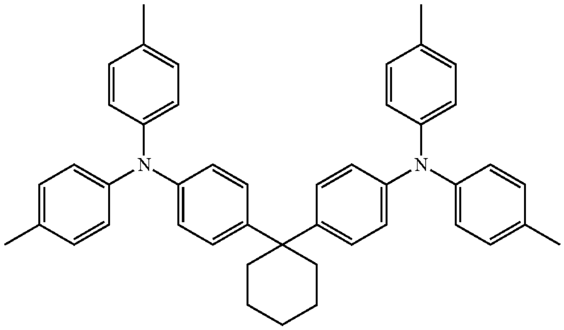

TAPC

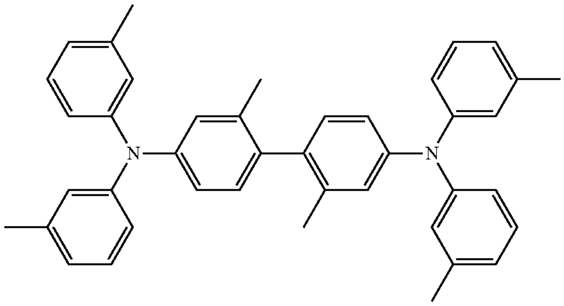

HMTPD

Formula 201

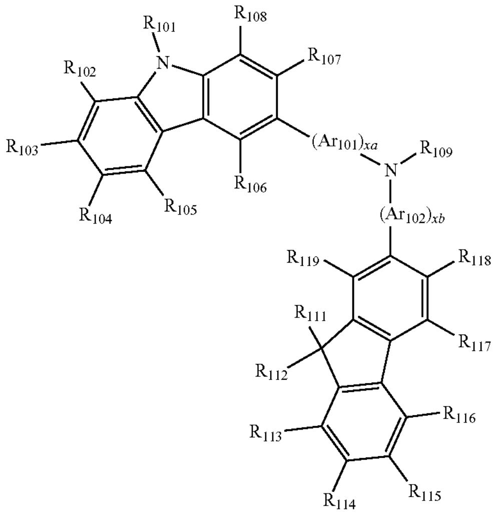

-continued

Formula 202

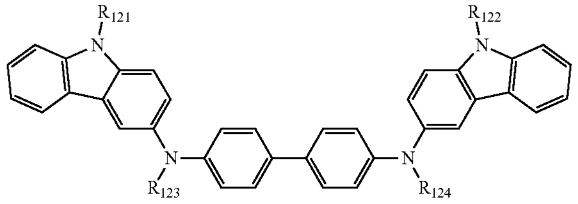

wherein, in Formula 201, $Ar_{101}$ and $Ar_{102}$ may each independently be a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, or a pentacenylene group, each unsubstituted or substituted with deuterium, —F, —Cl, —Br, —I, a hydroxyl group, a cyano group, a nitro group, an amino group, a $C_1$-$C_{60}$ alkyl group, a $C_2$-$C_{60}$ alkenyl group, a $C_2$-$C_{60}$ alkynyl group, a $C_1$-Coo alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, or any combination thereof.

In Formula 201, xa and xb may each independently be an integer from 0 to 5. In some embodiments, xa and xb may each independently be 0, 1, or 2. In some embodiments, xa may be 1, and xb may be 0.

In Formulae 201 and 202, $R_{101}$ to $R_{108}$, $R_{111}$ to $R_{119}$, and $R_{121}$ to $R_{124}$ may each independently be:

hydrogen, deuterium, —F, —Cl, —Br, —I, a hydroxyl group, a cyano group, a nitro group, an amino group, a $C_1$-$C_{10}$ alkyl group (e.g., a methyl group, an ethyl group, a propyl group, a butyl group, a pentyl group, or a hexyl group), or a $C_1$-$C_{10}$ alkoxy group (e.g., a methoxy group, an ethoxy group, a propoxy group, a butoxy group, or a pentoxy group);

a $C_1$-$C_{10}$ alkyl or a $C_1$-$C_{10}$ alkoxy group, each substituted with deuterium, —F, —Cl, —Br, —I, a hydroxyl group, a cyano group, a nitro group, an amino group, or any combination thereof; or a phenyl group, a naphthyl group, an anthracenyl group, a fluorenyl group, or a pyrenyl group, unsubstituted or substituted with each deuterium, —F, —Cl, —Br, —I, a hydroxyl group, a cyano group, a nitro group, an amino group, a $C_1$-$C_{10}$ alkyl group, a $C_1$-$C_{10}$ alkoxy group, or any combination thereof.

In Formula 201, $R_{199}$ may be a phenyl group, a naphthyl group, an anthracenyl group, or a pyridinyl group, each unsubstituted or substituted with deuterium, —F, —Cl, —Br, —I, a hydroxyl group, a cyano group, a nitro group, an amino group, a $C_1$-$C_{20}$ alkyl group, a $C_1$-$C_{20}$ alkoxy group, a phenyl group, a naphthyl group, an anthracenyl group, a pyridinyl group, or any combination thereof.

In some embodiments, the compound represented by Formula 201 may be represented by Formula 201A:

Formula 201A
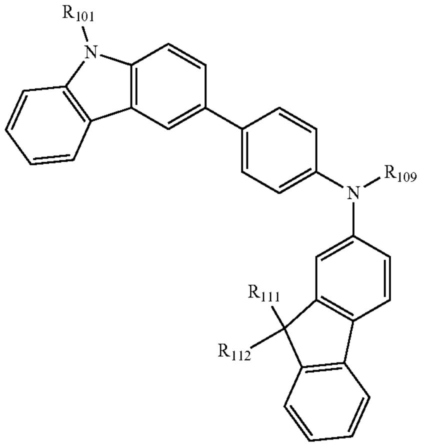
wherein, in Formula 201A, $R_{101}$, $R_{111}$, $R_{112}$, and $R_{109}$ may respectively be understood by referring to the descriptions of $R_{101}$, $R_{111}$, $R_{112}$, and $R_{109}$ provided herein.
For example, the hole transport region may include at least one of Compounds HT1 to HT20:
HT1
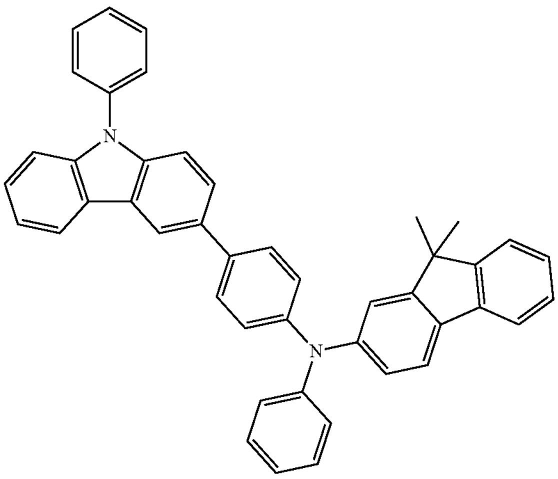
-continued
HT2
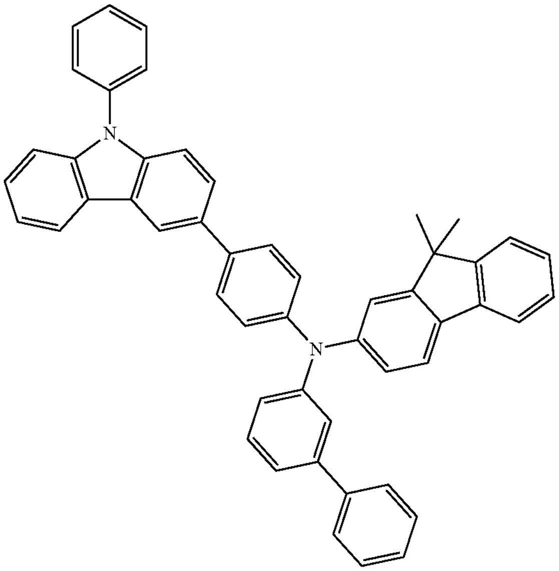
HT3
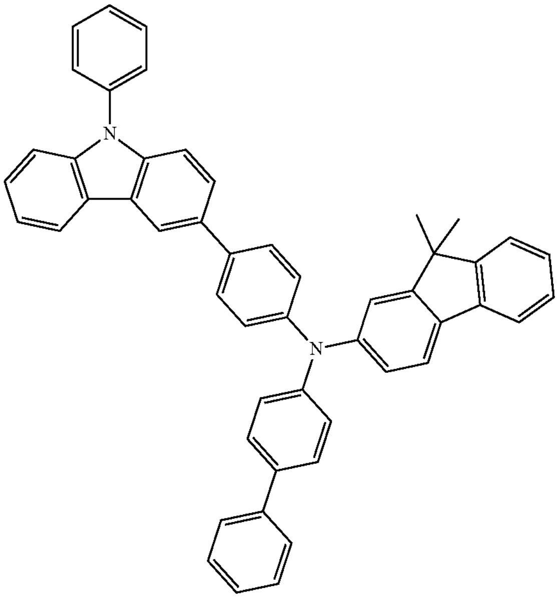

-continued
HT4
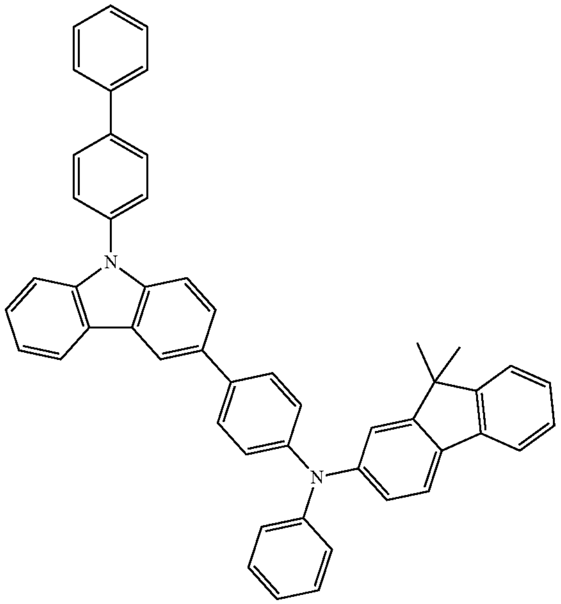
HT5
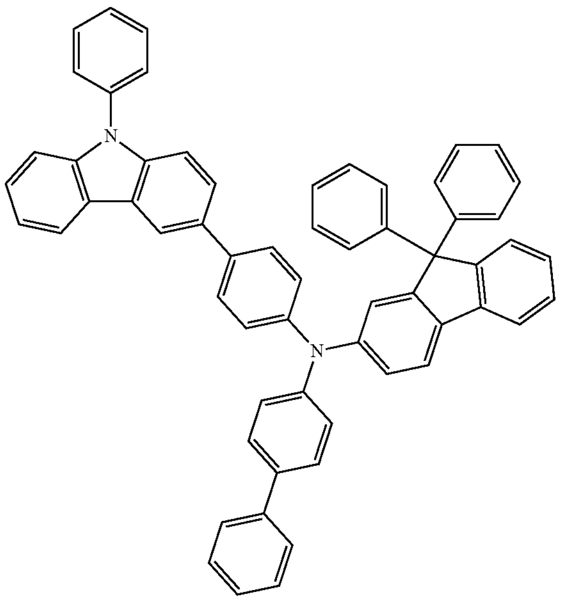
-continued
HT6
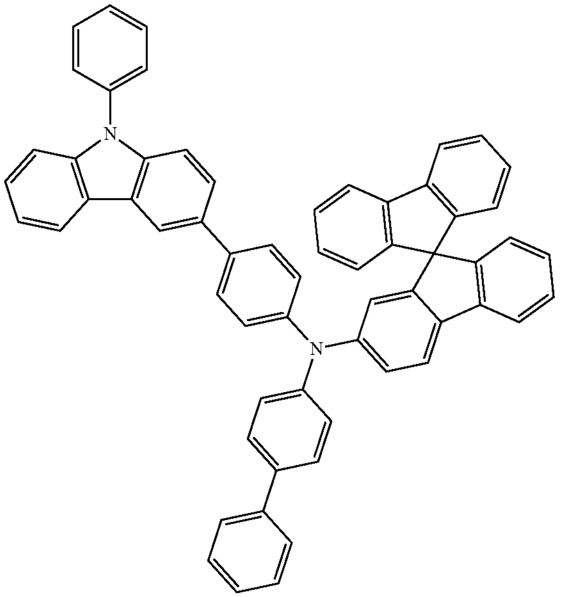
HT7
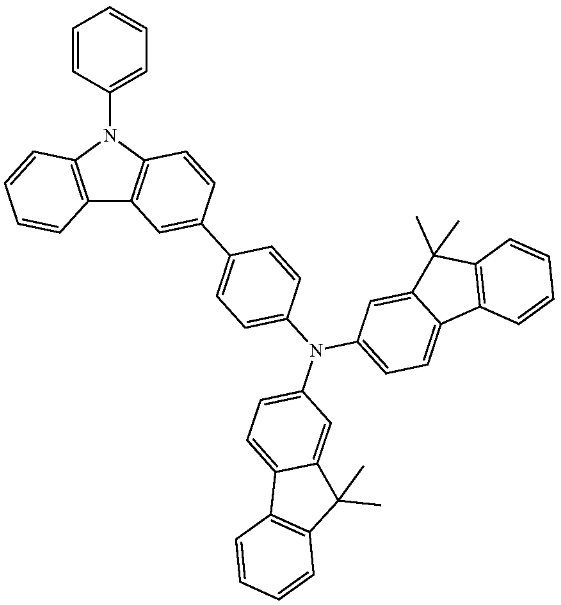

-continued
HT8
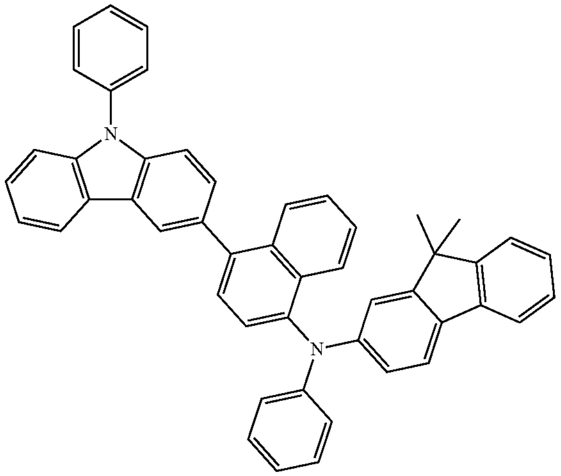
HT9
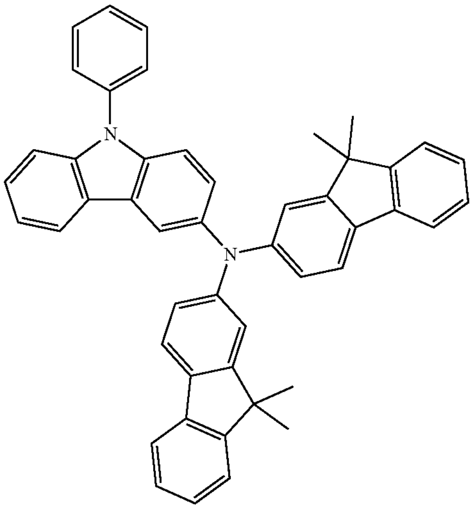
HT10
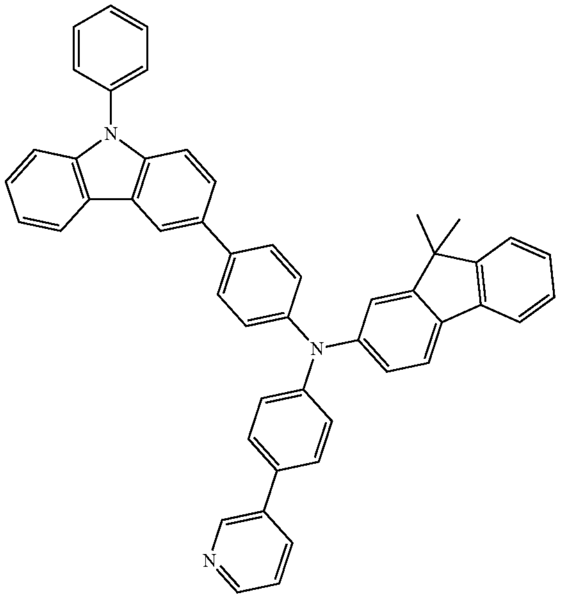
-continued
HT11
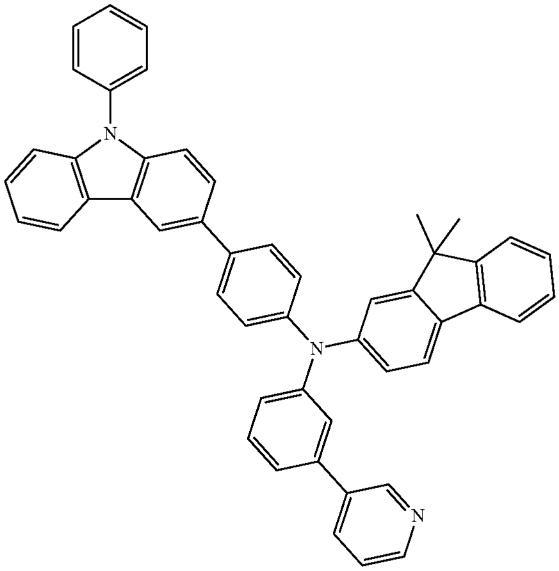
HT12
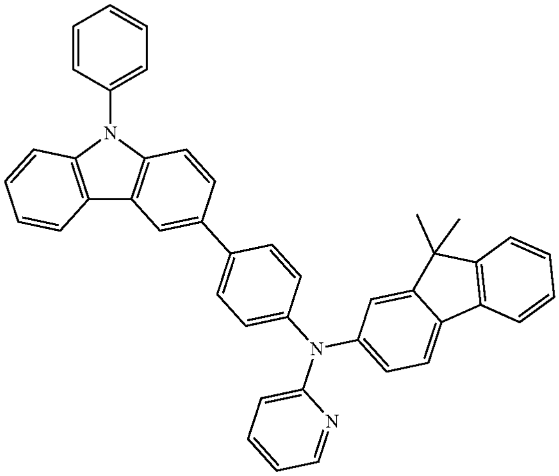
HT13
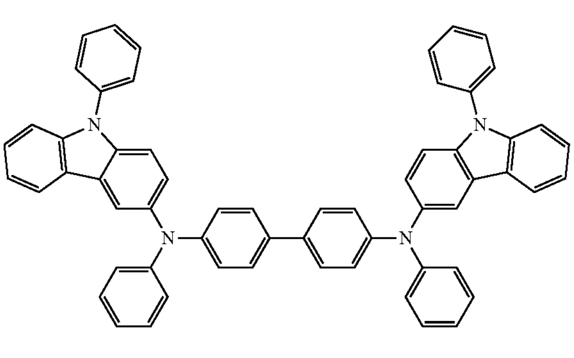

-continued

HT14

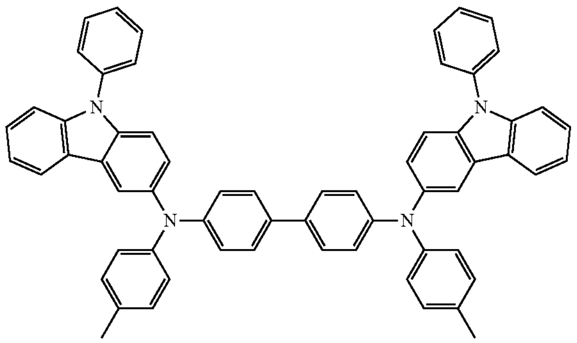

HT15

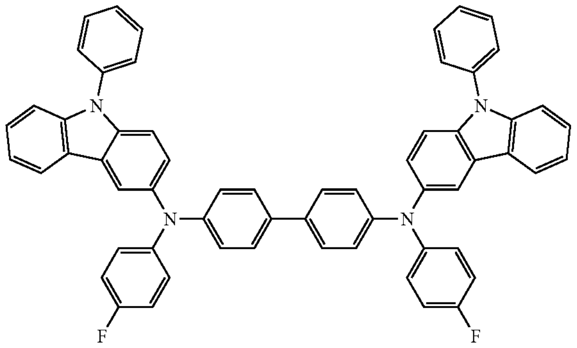

HT16

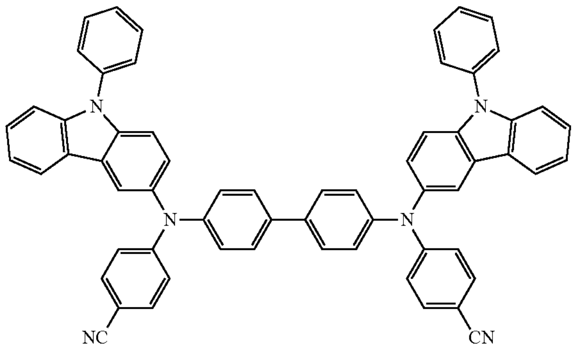

HT17

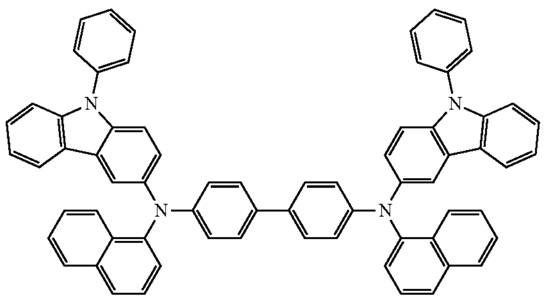

-continued

HT18

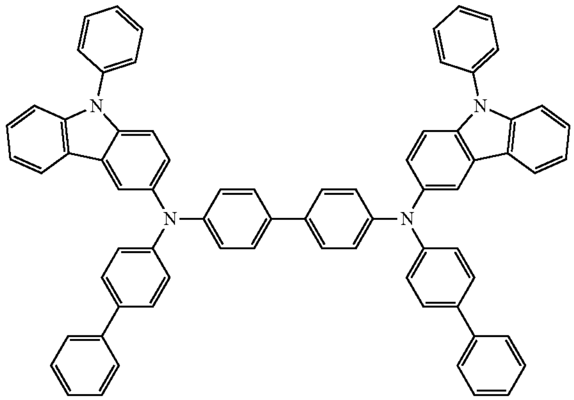

HT19

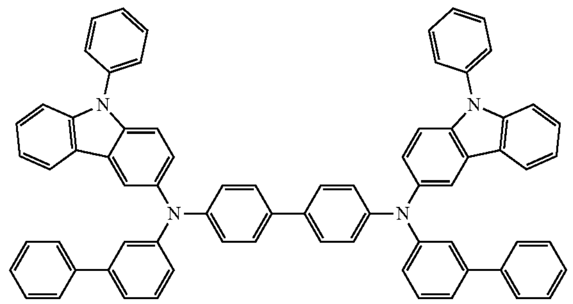

HT20

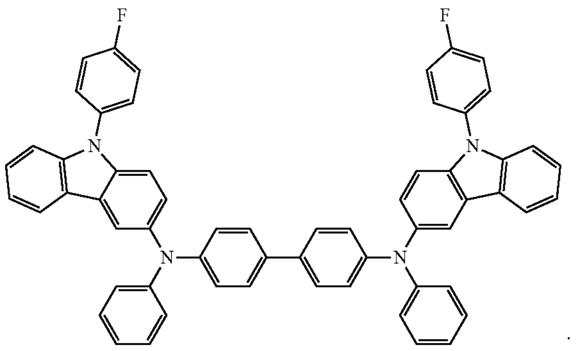

The thickness of the hole transport region may be in a range of about 100 Angstroms (A) to about 10,000 Å, for example, about 100 Å to about 1,000 Å. When the hole transport region includes a hole injection layer, a hole transport layer, an electron blocking layer, or any combination thereof, the thickness of the hole injection layer may be in a range of about 100 Å to about 10,000 Å, for example, about 100 Å to about 1,000 Å, the thickness of the hole transport layer may be in a range of about 50 Å to about 2,000 A, for example, about 100 Å to about 1,500 Å. When the thicknesses of the hole transport region, the hole injection layer, and the hole transport layer are within any of these ranges, excellent hole transport characteristics may be obtained without a substantial increase in driving voltage.

The hole transport region may include a charge generating material as well as the aforementioned materials, to improve conductive properties of the hole transport region. The charge generating material may be substantially homogeneously or non-homogeneously dispersed in the hole transport region.

The charge generating material may include, for example, a p-dopant. The p-dopant may be a quinone derivative, a metal oxide, a compound containing a cyano group, or any combination thereof. In some embodiments, the p-dopant may be a quinone derivative, such as tetracyanoquinodimethane (TCNQ), a 2,3,5,6-tetrafluoro-tetracyano-1,4-benzoquinonedimethane (F4-TCNQ), or F6-TCNNQ; a metal oxide, such as a tungsten oxide or a molybdenum oxide; a compound containing a cyano group, such as Compound HT-D1; or any combination thereof:

HT-D1

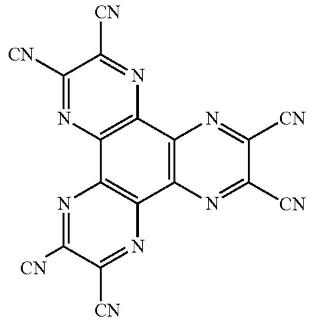

F4-TCNQ

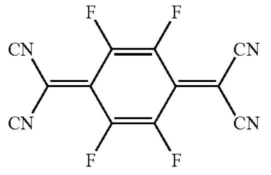

HT-D2

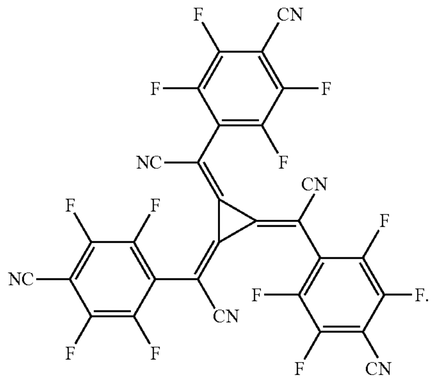

The hole transport region may further include a buffer layer.

The buffer layer may compensate for an optical resonance distance depending on a wavelength of light emitted from the emission layer to improve the efficiency of an organic light-emitting device.

When the hole transport region includes an electron blocking layer, a material for forming the electron blocking layer may include the material for forming a hole transport region, the host material described herein or any combination thereof. In some embodiments, when the hole transport region includes an electron blocking layer, mCP described herein may be used for forming the electron blocking layer.

mCP

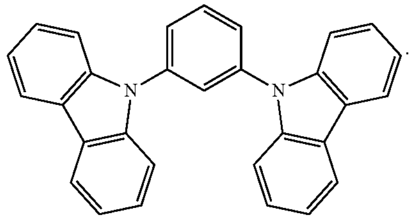

In some embodiments, a host included in the emission layer may be used as a material for forming the electron blocking layer.

The emission layer may be formed on the hole transport region by using one or more suitable methods, such as vacuum deposition, spin coating, casting, or LB deposition. When the emission layer is formed by vacuum deposition or spin coating, vacuum deposition and coating conditions for forming the emission layer may be generally similar to those conditions for forming a hole injection layer, although the conditions may vary depending on a compound that is used.

When the organic light-emitting device is a full-color organic light-emitting device, the emission layer may be patterned into a red emission layer, a green emission layer, and a blue emission layer. In some embodiments, the emission layer may have a structure in which the red emission layer, the green emission layer, and/or the blue emission layer are layered to emit white light. In some embodiments, the structure of the emission layer may vary.

The emission layer may include a fluorescent compound that may satisfy conditions described herein. The emission layer may consist of the fluorescent compound or may further include any suitable host, in addition to the fluorescent compound. The fluorescent compound may emit blue or deep-blue light. The host may be understood by referring to the description of the host provided herein.

The thickness of the emission layer may be in a range of about 100 Å to about 1,000 Å, and in some embodiments, about 200 Å to about 600 Å. When the thickness of the emission layer is within any of these ranges, improved luminescence characteristics may be obtained without a substantial increase in driving voltage.

Next, an electron transport region may be formed on the emission layer.

The electron transport region may include a hole blocking layer, an electron transport layer, an electron injection layer, or a combination thereof.

In some embodiments, the electron transport region may have a hole blocking layer/an electron transport layer/an electron injection layer structure or an electron transport layer/an electron injection layer structure. The electron transport layer may have a single-layered structure or a multi-layered structure including two or more different materials.

The conditions for forming a hole blocking layer, an electron transport layer, and an electron injection layer may be inferred based on the conditions for forming the hole injection layer.

When the electron transport region includes a hole blocking layer, the hole blocking layer may include, for example, BCP, Bphen, BAlq, or any combination thereof:

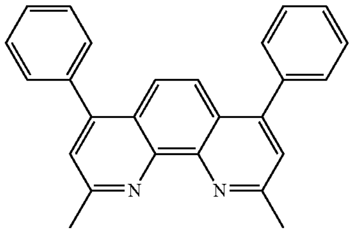

BCP

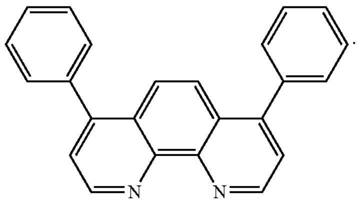

Bphen

In some embodiments, the host used in the emission layer may be used as a material for forming the hole blocking layer.

The thickness of the hole blocking layer may be in a range of about 20 Å to about 1,000 Å, for example, about 30 Å to about 600 Å. When the thickness of the hole blocking layer is within any of these ranges, excellent hole blocking characteristics may be obtained without a substantial increase in driving voltage.

The electron transport layer may include BCP, Bphen, TP Bi, $Alq_3$, BAlq, TAZ, NTAZ, or any combination thereof:

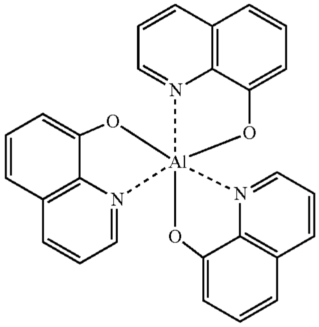

$Alq_3$

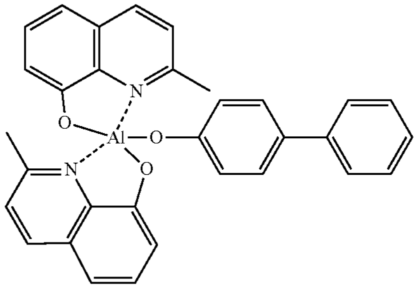

BAlq

-continued

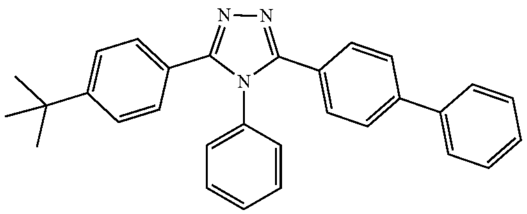

TAZ

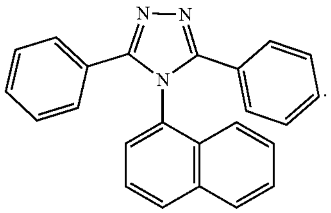

NTAZ

In some embodiments, the electron transport layer may include at least one of Compounds ET1 to ET25.

ET1

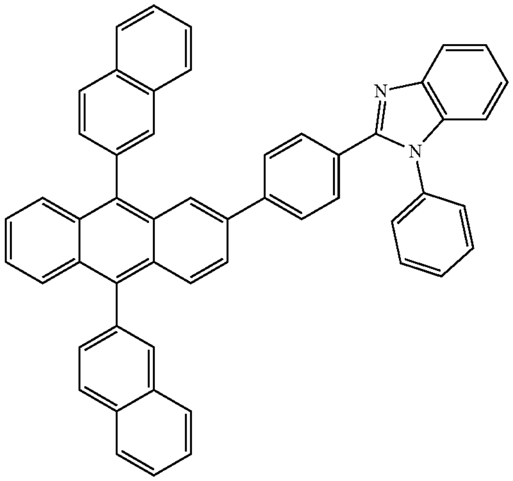

ET2

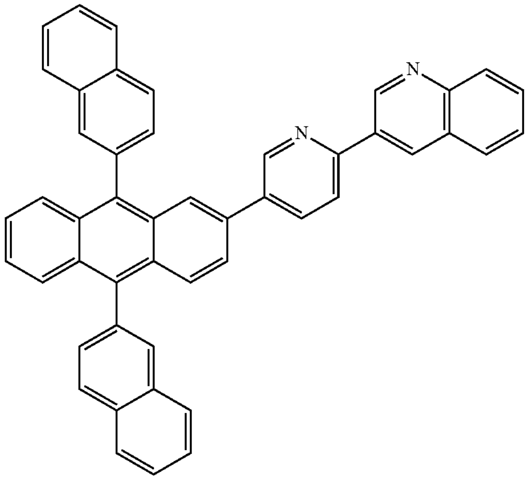

-continued
ET3
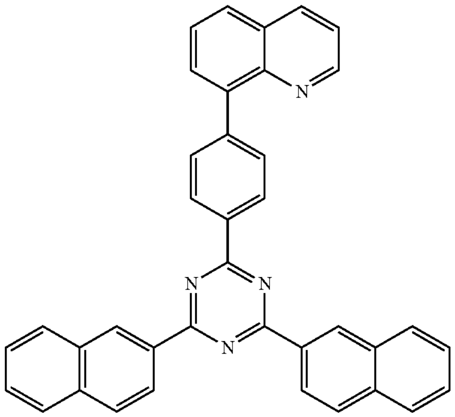
ET4
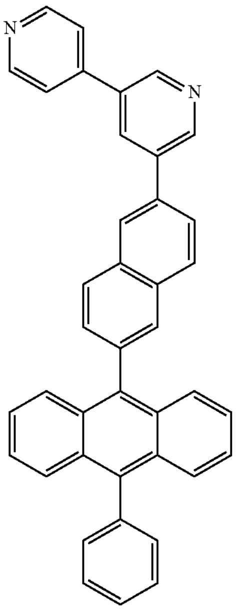
ET5
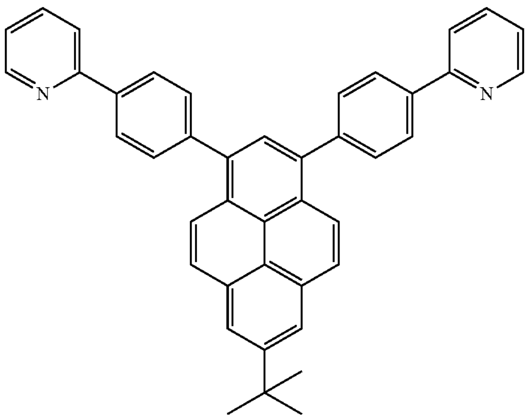
-continued
ET6
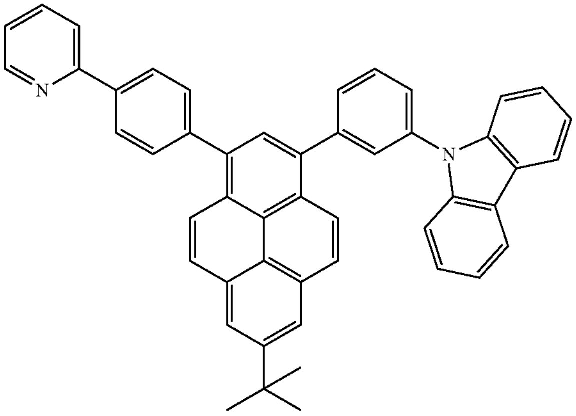
ET7
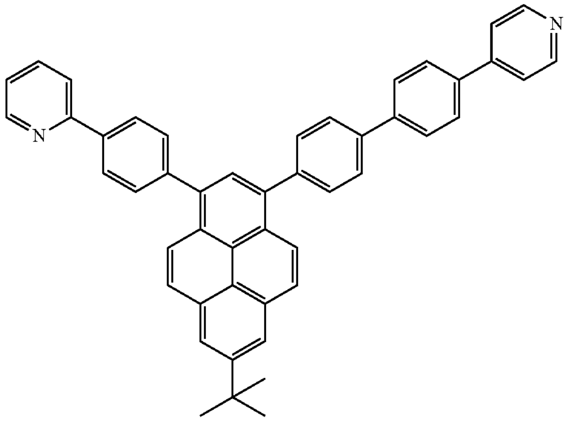
ET8
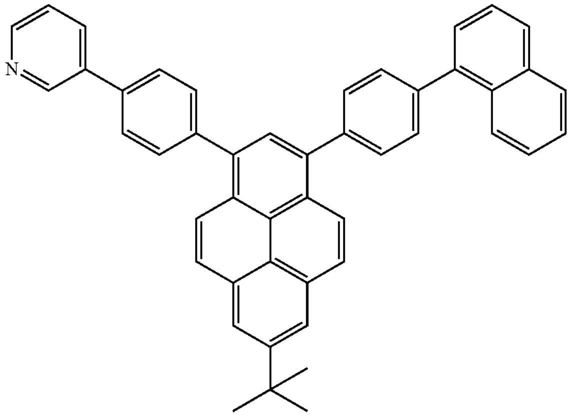

-continued
ET9
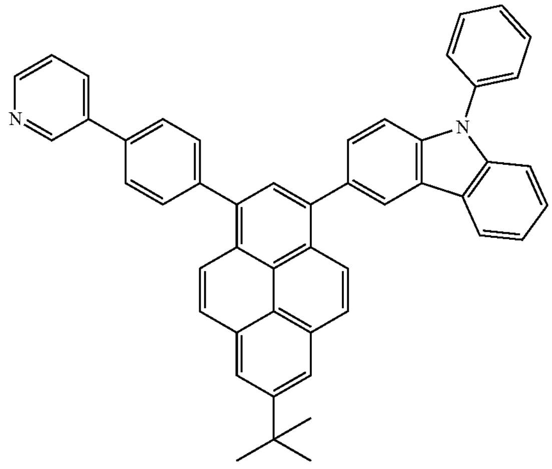
ET10
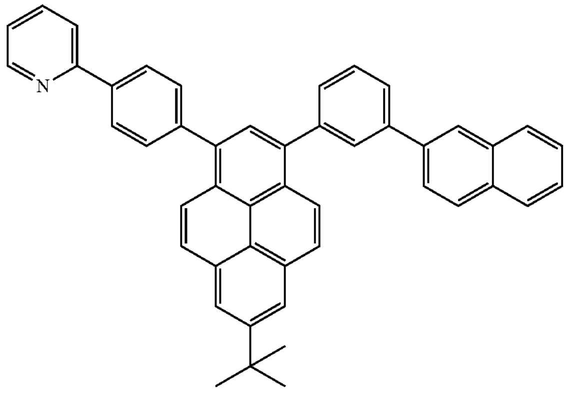
ET11
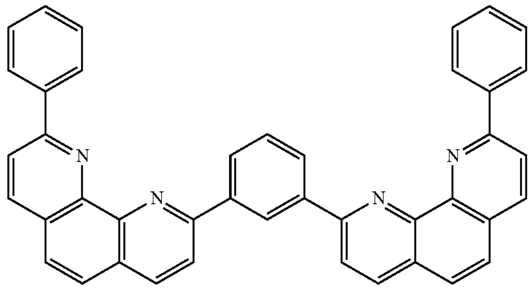
ET12
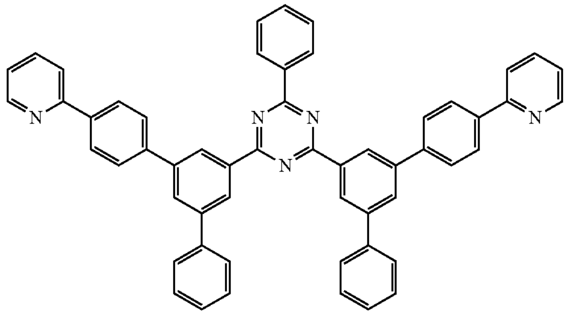
-continued
ET13
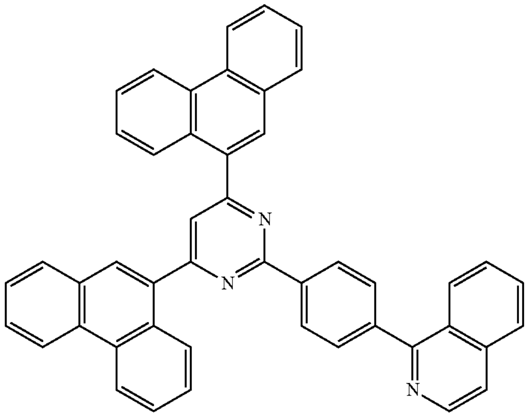
ET14
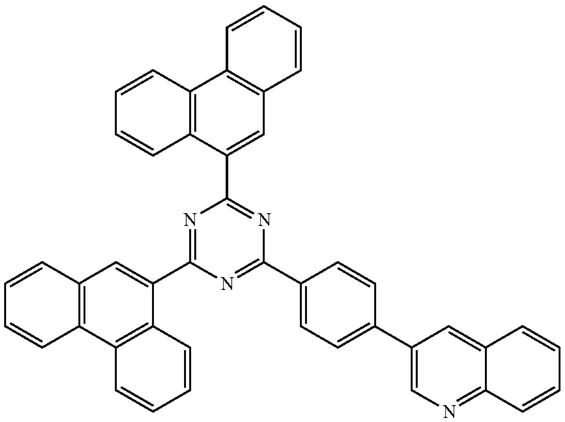
ET15
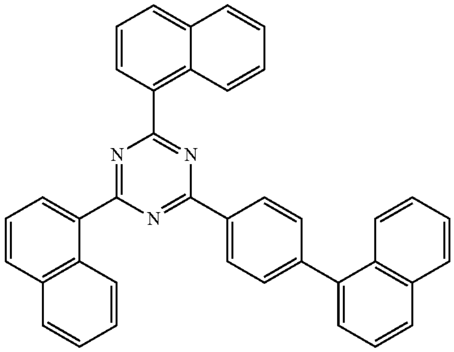

-continued
ET16
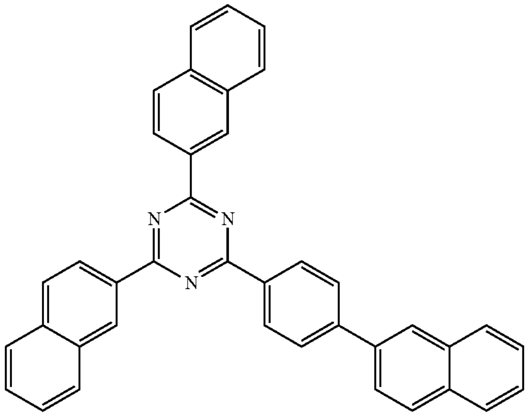
ET17
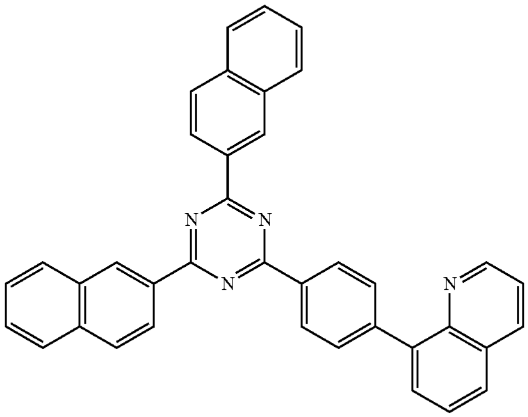
ET18
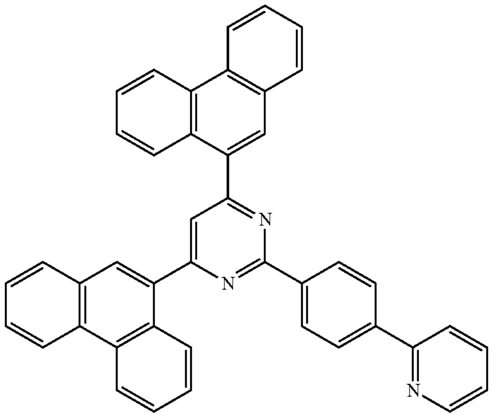
-continued
ET19
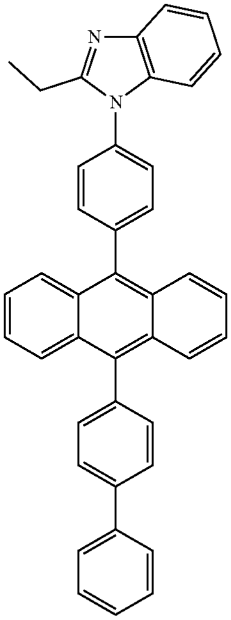
ET20
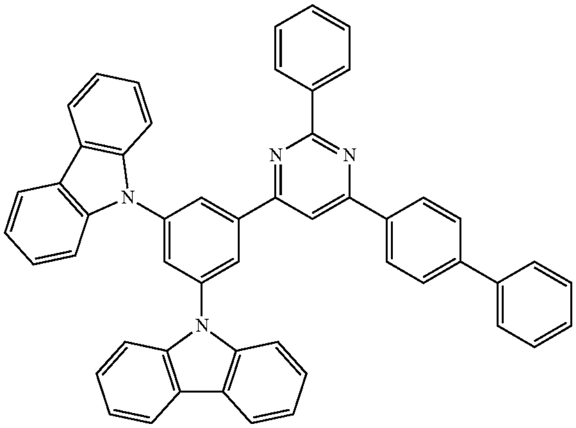
ET21
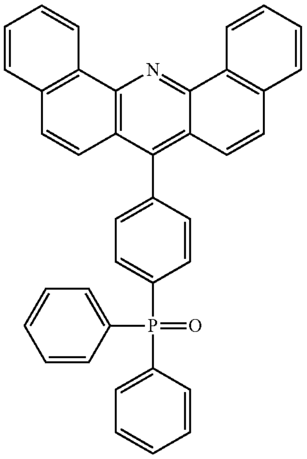

-continued

ET22

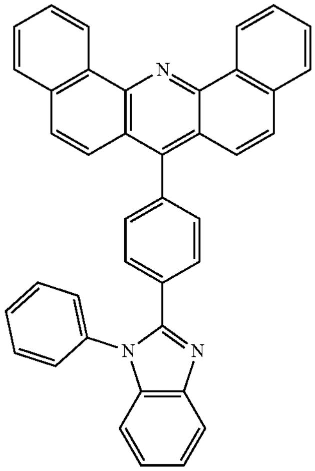

ET23

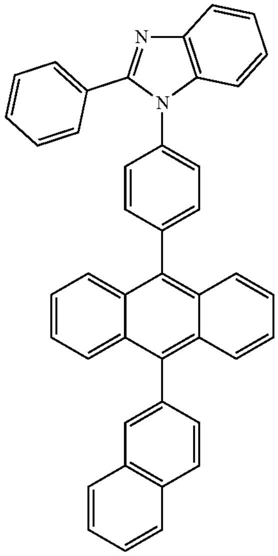

ET24

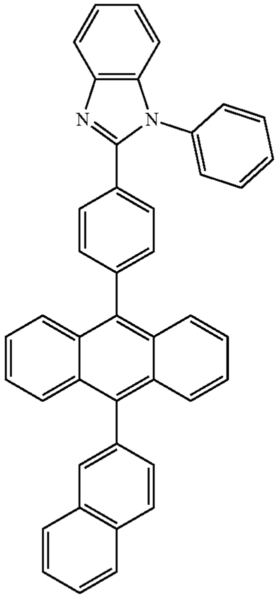

-continued

ET25

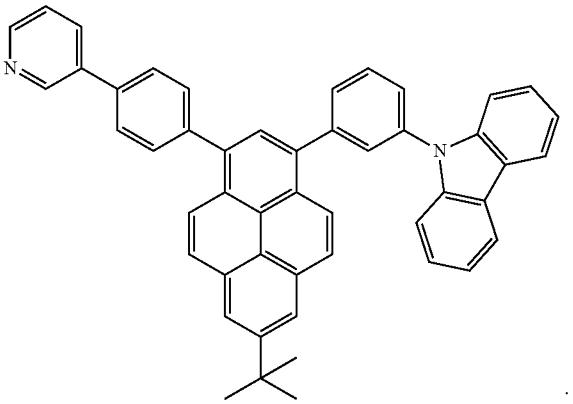

The thickness of the electron transport layer may be in a range of about 100 Å to about 1,000 Å, and in some embodiments, about 150 Å to about 500 Å. When the thickness of the electron transport layer is within any of these ranges, excellent electron transport characteristics may be obtained without a substantial increase in driving voltage.

The electron transport layer may further include a material containing metal, in addition to the materials described above.

The material containing metal may include a Li complex. The Li complex may include, e.g., Compound ET-D1 (LiQ) or Compound ET-D2:

ET-D1

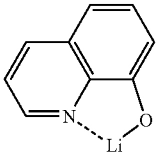

ET-D2

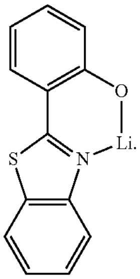

The electron transport region may include an electron injection layer that facilitates electron injection from the second electrode 19.

The electron injection layer may include LiF, NaCl, CsF, $Li_2O$, BaO, Compound ET-D1, Compound ET-D2, or any combination thereof.

The thickness of the electron injection layer may be in a range of about 1 Å to about 100 Å, and in some embodiments, about 3 Å to about 90 Å. When the thickness of the electron injection layer is within any of these ranges, excellent electron injection characteristics may be obtained without a substantial increase in driving voltage.

The second electrode 19 may be on the organic layer 15. The second electrode 19 may be a cathode. A material for forming the second electrode 19 may be a material with a relatively low work function, such as a metal, an alloy, an electrically conductive compound, or any combination thereof. Examples of the material for forming the second electrode 19 may include lithium (Li), magnesium (Mg), aluminum (Al), silver (Ag), aluminum-lithium (Al—Li), calcium (Ca), magnesium-indium (Mg—In), and magnesium-silver (Mg—Ag). In some embodiments, ITO or IZO may be used to form a transmissive second electrode 19 to manufacture a top emission light-emitting device. In some embodiments, the material for forming the second electrode 19 may vary.

According to an aspect of another embodiment, an electronic apparatus may include the light-emitting device. Thus, an electronic apparatus including the light-emitting device may be provided. The electronic apparatus may include, for example, a display, lighting, a sensor, or the like.

According to one or more embodiments, a fluorescent compound having at least one carbonyl group, wherein, upon excitation, excitons in a $^3$n-π* excited state of the fluorescent compound may migrate to a $^1$π-π* excited state of the fluorescent compound by reverse intersystem crossing with a Rate (rISC), excitons in the $^3$n-π* excited state of the fluorescent compound may migrate to a $^3$π-π* excited state of the fluorescent compound by reverse internal conversion with a Rate (IC), which may undergo radiative transition to a ground state to resulting in emission of light via fluorescence, a ratio of Rate (rISC) to Rate (IC) may be 0.5 or greater, excitons in a $^1$π-π* excited state of the fluorescent compound may undergo radiative transition to a ground state to thereby emit fluorescence, Rate (rISC) may be evaluated by Equation 1, and Rate (IC) may be evaluated by Equation 2, as described herein.

The fluorescent compound may be understood by referring to the description of the fluorescent compound provided herein.

The term "$C_1$-$C_{60}$ alkyl group" as used herein refers to a linear or branched saturated aliphatic hydrocarbon monovalent group having 1 to 60 carbon atoms, and the term "$C_1$-$C_{60}$ alkylene group" as used herein refers to a divalent group having the same structure as the $C_1$-$C_{60}$ alkyl group.

Examples of the $C_1$-$C_{60}$ alkyl group, the $C_1$-$C_{20}$ alkyl group, and/or the $C_1$-$C_{10}$ alkyl group alkyl group include a methyl group, an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, or a tert-decyl group, each unsubstituted or substituted with a methyl group, an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, or any combination thereof.

The term "$C_1$-$C_{60}$ alkoxy group" as used herein refers to a monovalent group represented by —$OA_{101}$ (wherein $A_{101}$ is a $C_1$-$C_{60}$ alkyl group). Examples thereof include a methoxy group, an ethoxy group, a propoxy group, a butoxy group, and a pentoxy group.

The term "$C_2$-$C_{60}$ alkenyl group" as used herein refers to a group formed by including at least one carbon-carbon double bond in the middle or at the terminus of the $C_2$-$C_{60}$ alkyl group. Examples thereof include an ethenyl group, a propenyl group, and a butenyl group. The term "$C_2$-$C_{60}$ alkenylene group" as used herein refers to a divalent group having substantially the same structure as the $C_2$-$C_{60}$ alkenyl group.

The term "$C_2$-$C_{60}$ alkynyl group" as used herein refers to a group formed by including at least one carbon-carbon triple bond in the middle or at the terminus of the $C_2$-$C_{60}$ alkyl group. Examples thereof include an ethenyl group and a propenyl group. The term "$C_2$-$C_{60}$ alkynylene group" as used herein refers to a divalent group having substantially the same structure as the $C_2$-$C_{60}$ alkynyl group.

The term "$C_3$-$C_{10}$ cycloalkyl group" as used herein refers to a monovalent saturated hydrocarbon cyclic group having 3 to 10 carbon atoms. The term "$C_3$-$C_{10}$ cycloalkylene group" as used herein refers to a divalent group having the same structure as the $C_3$-$C_{10}$ cycloalkyl group.

Examples of the $C_3$-$C_{10}$ cycloalkyl group as used herein include a cyclopropyl group, a cyclobutyl group, a cyclopentyl group, a cyclohexyl group, a cycloheptyl group, a cyclooctyl group, an adamantanyl group, a norbornanyl (bicyclo[2.2.1]heptyl) group, a bicyclo[1.1.1]pentyl group, a bicyclo[2.1.1]hexyl group, and a bicyclo[2.2.2]octyl group.

The term "$C_1$-$C_{10}$ heterocycloalkyl group" as used herein refers to a monovalent saturated cyclic group having 1 to 10 carbon atoms and at least one heteroatom of N, O, P, Si, S, Se, Ge, and B as a ring-forming atom. The term "$C_1$-$C_{10}$ heterocycloalkylene group" as used herein refers to a divalent group having the same structure as the $C_1$-$C_{10}$ heterocycloalkyl group.

Examples of the $C_1$-$C_{10}$ heterocycloalkyl group as used herein may include a silolanyl group, a silinanyl group, a tetrahydrofuranyl group, a tetrahydro-2H-pyranyl group, or a tetrahydrothiophenyl group.

The term "$C_3$-$C_{10}$ cycloalkenyl group" as used herein refers to a monovalent monocyclic group including 3 to 10 carbon atoms and at least one carbon-carbon double bond in its ring, wherein the molecular structure as a whole is non-aromatic. Examples thereof include a cyclopentenyl group, a cyclohexenyl group, and a cycloheptenyl group. The term "$C_3$-$C_{10}$ cycloalkenylene group" as used herein refers to a divalent group having substantially the same structure as the $C_3$-$C_{10}$ cycloalkenyl group.

The term "$C_1$-$C_{10}$ heterocycloalkenyl group" as used herein refers to a monovalent cyclic group including at least one heteroatom of N, O, P, Si, S, Se, Ge, and B as a ring-forming atom, 1 to 10 carbon atoms, and at least one double bond in its ring. Examples of the $C_1$-$C_{10}$ heterocycloalkenyl group include a 2,3-dihydrofuranyl group and a 2,3-dihydrothiophenyl group. The term "$C_1$-$C_{10}$ heterocycloalkylene group" as used herein refers to a divalent group having substantially the same structure as the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms. The term "$C_6$-$C_{60}$ arylene group" as used herein refers to a divalent group having a carbocyclic aromatic system having 6 to 60 carbon atoms. Examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and a $C_6$-$C_{60}$ arylene group each include at least two rings, the at least two rings may be fused.

The term "$C_1$-$C_{60}$ heteroaryl group" as used herein refers to a monovalent group having a heterocyclic aromatic system having at least one heteroatom selected from N, O, P, Si, S, Se, Ge, and B as a ring-forming atom and 1 to 60 carbon atoms. The term "$C_1$-$C_{60}$ heteroarylene group" as used herein refers to a divalent group having a heterocyclic aromatic system having at least one heteroatom selected from N, O, P, Si, S, Se, Ge, and B as a ring-forming atom and 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include at least two rings, the at least two rings may be fused.

The term "carbonyl group" us used herein refers to a divalent group represented by *—C(═O)—*' (wherein * and *' may each indicate a binding site to an adjacent atom).

The term "$C_6$-$C_{60}$ aryloxy group" as used herein refers to —$OA_{102}$ (wherein $A_{102}$ is a $C_6$-$C_{60}$ aryl group). The term "$C_6$-$C_{60}$ arylthio group" as used herein refers to —$SA_{103}$ (wherein $A_{103}$ is a $C_6$-$C_{60}$ aryl group). The term "$C_1$-$C_{60}$ alkylthio group" as used herein refers to —$SA_{104}$ (wherein $A_{104}$ is a Cl—CH alkyl group).

The term "monovalent non-aromatic condensed polycyclic group" as used herein refers to a monovalent group that has two or more condensed rings and only carbon atoms (e.g., the number of carbon atoms may be in a range of 8 to 60) as ring-forming atoms, wherein the molecular structure as a whole is non-aromatic. Examples of the monovalent non-aromatic condensed polycyclic group include a fluorenyl group. The term "divalent non-aromatic condensed polycyclic group" as used herein refers to a divalent group having substantially the same structure as the monovalent non-aromatic condensed polycyclic group.

The term "monovalent non-aromatic condensed heteropolycyclic group" as used herein refers to a monovalent group that has two or more condensed rings and at least one heteroatom selected from N, O, P, Si, S, Se, Ge, and B and carbon atoms (e.g., the number of carbon atoms may be in a range of 1 to 60) as ring-forming atoms, wherein the molecular structure as a whole is non-aromatic. Examples of the monovalent non-aromatic condensed heteropolycyclic group include a carbazolyl group. The term "divalent non-aromatic condensed heteropolycyclic group" as used herein refers to a divalent group having substantially the same structure as the monovalent non-aromatic condensed heteropolycyclic group.

The term "$C_5$-$C_{60}$ carbocyclic group" as used herein refers to a saturated or unsaturated cyclic group including 5 to 60 carbon atoms as ring-forming atoms. The $C_5$-$C_{60}$ carbocyclic group may be a monocyclic group or a polycyclic group. Examples of the "$C_5$-$C_{30}$ carbocyclic group (unsubstituted or substituted with at least one $R_{10a}$)" may include an adamantane group, a norbornene group, a bicyclo[1.1.1]pentane group, a bicyclo[2.1.1]hexane group, a bicyclo[2.2.1]heptane group (a norbornane group), a bicyclo[2.2.2]octane group, a cyclopentane group, a cyclohexane group, a cyclohexene group, a benzene group, a naphthalene group, an anthracene group, a phenanthrene group, a triphenylene group, a pyrene group, a chrysene group, a 1,2,3,4-tetrahydronaphthalene group, a cyclopentadiene group, or a fluorene group, (each unsubstituted or substituted with at least one $R_{10a}$).

The term "$C_1$-$C_{60}$ heterocyclic group" as used herein refers to saturated or unsaturated cyclic group including 1 to 60 carbon atoms and at least one heteroatom selected from N, O, P, Si, S, Se, Ge, and B as ring-forming atoms. The $C_1$-$C_{60}$ heterocyclic group may be a monocyclic group or a polycyclic group. Examples of the "$C_1$-$C_{30}$ heterocyclic group (unsubstituted or substituted with at least one $R_{10a}$)" may include a thiophene group, a furan group, a pyrrole group, a silole group, a borole group, a phosphole group, a selenophene group, a germole group, a benzothiophene group, a benzofuran group, an indole group, a benzosilole group, a benzoborole group, a benzophosphole group, a benzoselenophene group, a benzogermole group, a dibenzothiophene group, a dibenzofuran group, a carbazole group, a dibenzosilole group, a dibenzoborole group, a dibenzophosphole group, a dibenzoselenophene group, a dibenzogermole group, a dibenzothiophene 5-oxide group, a 9H-fluorene-9-one group, a dibenzothiophene 5,5-dioxide group, an azabenzothiophene group, an azabenzofuran group, an azaindole group, an azaindene group, an azabenzosilole group, an azabenzoborole group, an azabenzophosphole group, an azabenzoselenophene group, an azabenzogermole group, an azadibenzothiophene group, an azadibenzofuran group, an azacarbazole group, an azafluorene group, an azadibenzosilole group, an azadibenzoborole group, an azadibenzophosphole group, an azadibenzoselenophene group, an azadibenzogermole group, an azadibenzothiophene 5-oxide group, an aza-9H-fluoren-9-one group, an azadibenzothiophene 5,5-dioxide group, a pyridine group, a pyrimidine group, a pyrazine group, a pyridazine group, a triazine group, a quinoline group, an isoquinoline group, a quinoxaline group, a quinazoline group, a phenanthroline group, a pyrazole group, an imidazole group, a triazole group, an oxazole group, an isooxazole group, a thiazole group, an isothiazole group, an oxadiazole group, a thiadiazole group, a benzopyrazole group, a benzimidazole group, a benzoxazole group, a benzothiazole group, a benzoxadiazole group, a benzothiadiazole group, a 5,6,7,8-tetrahydroisoquinoline group, or a 5,6,7,8-tetrahydroquinoline group, (each unsubstituted or substituted with at least one $R_{10a}$).

Examples of the "$C_5$-$C_{60}$ carbocyclic group" and the "$C_1$-$C_{60}$ heterocyclic group" as used herein include i) a first ring, ii) a second ring, iii) a condensed ring in which at least two first rings are condensed, iv) a condensed ring in which at least two second rings are condensed, or v) a condensed ring in which at least one first ring and at least one second ring are condensed, the first ring may be a cyclopentane group, a cyclopentene group, a furan group, a thiophene group, a pyrrole group, a silole group, a borole group, a phosphole group, a germole group, a selenophene group, an oxazole group, an oxadiazole group, an oxatriazole group, a thiazole group, a thiadiazole group, a thiatriazole group, a pyrazole group, an imidazole group, a triazole group, a tetrazole group, or an azasilole group, and the second ring may be an adamantane group, a norbornane group, a norbornene group, a cyclohexane group, a cyclohexene group, a benzene group, a pyridine group, a pyrimidine group, a pyrazine group, a pyridazine group, or a triazine group.

In the presented specification, at least one substituent of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), —B($Q_{16}$)($Q_{17}$), —P(═O)($Q_{18}$)($Q_{19}$), or any combination thereof;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), —B($Q_{26}$)($Q_{27}$), —P(═O)($Q_{28}$)($Q_{29}$), or any combination thereof; or —N($Q_{31}$)($Q_{32}$), —Si($Q_{33}$)($Q_{34}$)($Q_{35}$), —B($Q_{36}$)($Q_{37}$), or —P(═O)($Q_{38}$)($Q_{39}$), wherein Qi to $Q_9$, $Q_{11}$ to $Q_{19}$, $Q_{21}$ to $Q_{29}$, and $Q_{31}$ to $Q_{39}$ may each independently be hydrogen, deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one selected from deuterium; a $C_1$-$C_{60}$ alkyl group; and a $C_6$-$C_{60}$ aryl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one selected from deuterium; a $C_1$-$C_{60}$ alkyl group; and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group.

The term "room temperature" as used herein refers to a temperature of about 25° C.

Hereinafter, a compound and an organic light-emitting device according to an embodiment will be described in detail with reference to Synthesis Examples and Examples, however, the present disclosure is not limited thereto. The wording "B was used instead of A" used in describing Synthesis Examples means that an amount of B used was identical to an amount of A used based on molar equivalence.

EXAMPLES

Synthesis Example of Compound 1

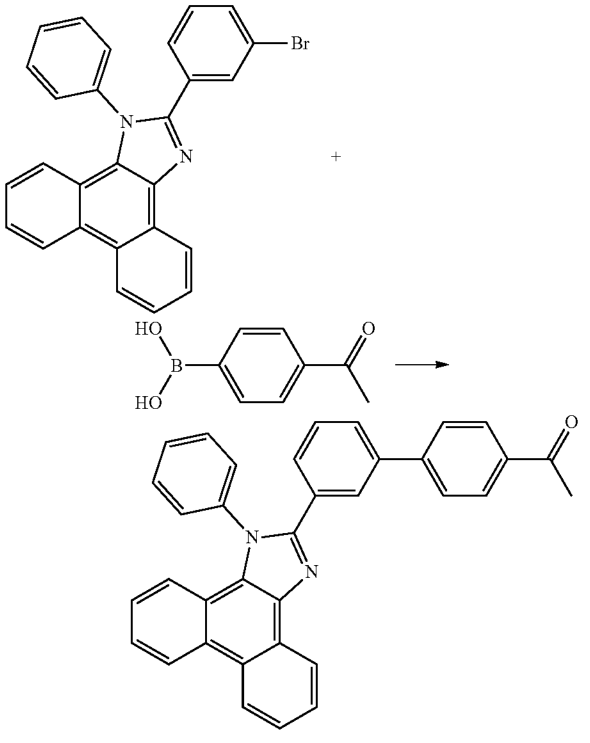

1

1.00 grams (g)(2.23 millimoles (mmol)) of 2-(3-bromophenyl)-1-phenyl-1H-phenanthro[9,10-d]imidazole, 0.55 g (3.34 mmol) of 4-acetylphenylboronic acid, 0.25 g (0.22 mmol) of tetrakis(triphenylphosphine)palladium(0), and 0.92 g (6.69 mmol) of potassium carbonate were added to a 500 mL-round-bottom flask. Then, 100 milliliters (mL) of toluene, 100 mL of ethanol, and 50 mL of water were added to the flask, followed by stirring vigorously under an argon atmosphere at a temperature of 100° C. for 48 hours. The mixture was permitted to cool to room temperature. The solvent was concentrated under reduced pressure to obtain a residue. Water was added to the residue, followed by an extraction of the aqueous mixture with dichloromethane. The resulting organic layer was dried using anhydrous magnesium sulfate, followed by a filtration to remove magnesium sulfate. The organic layer was concentrated under reduced pressure to obtain a residue. The residue was purified using column chromatography (dichloromethane: hexane=4:1) to obtain 0.58 g of Compound 1 (white solid, 53% of yield). $^{1}$H-NMR (300 MHz, $CD_2Cl_2$) δ=2.62 (s, 3H), 7.23-7.33 (m, 2H), 7.43-7.57 (m, 4H), 7.60-7.80 (m, 10H), 8.00 (dd, J=1.8 Hz, 6.6 Hz, 2H), 8.73-8.84 (m, 3H) ppm; $^{13}$C-NMR (100 MHz, $CD_2Cl_2$) δ=26.5, 121.0, 122.5, 123.1, 123.2, 124.1, 125.0, 125.6, 126.4, 127.1, 127.3, 127.4, 128.0, 128.2, 128.3, 128.7, 128.9, 129.1, 129.2, 130.0, 130.4, 131.3, 136.1, 137.3, 138.9, 139.6, 144.8, 150.3, 197.3 ppm Synthesis Example of Compound 2

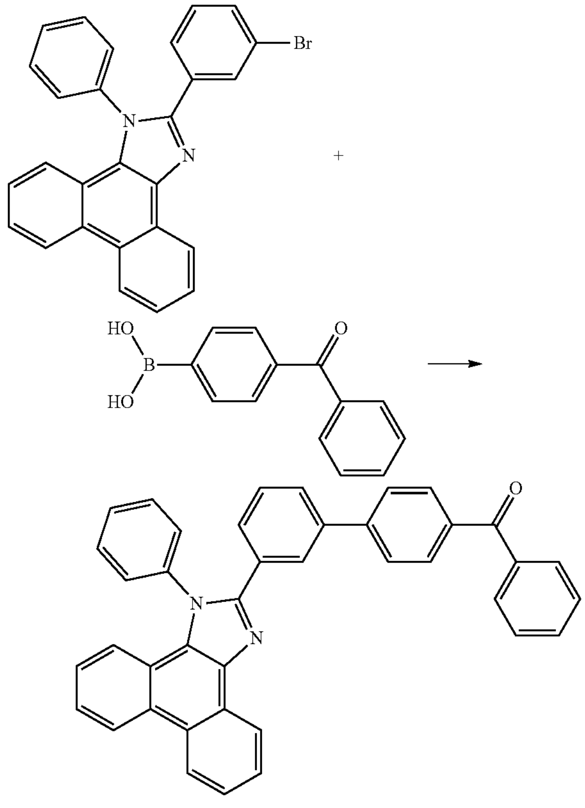

2

1.20 g (2.67 mmol) of 2-(3-bromophenyl)-1-phenyl-1H-phenanthro[9,10-d]imidazole, 0.91 g (4.00 mmol) of 4-benzoylphenylboronic acid, 0.31 g (0.27 mmol) of tetrakis (triphenylphosphine)palladium(0), and 1.11 g (8.01 mmol) of potassium carbonate were added to a 500 mL-round-bottom flask. Then, 100 mL of toluene, 100 mL of ethanol, and 50 mL of water were added to the flask, followed by stirring vigorously under an argon atmosphere at a temperature of 100° C. for 48 hours. The mixture was allowed to cool to room temperature. Then, the solvent was concentrated under reduced pressure to obtain a residue. Water was added to the residue, and the aqueous mixture extracted using dichloromethane. The resulting organic layer was dried using anhydrous magnesium sulfate and filtered to remove magnesium sulfate. The organic layer was concentrated under reduced pressure to obtain a residue. The residue was purified using column chromatography (dichloromethane:hexane=4:1) to obtain 0.97 g of Compound 2 (white solid, 66% of yield).

$^{1}$H-NMR (300 MHz, $CD_2Cl_2$) δ=7.24 (m, 2H), 7.45 (d, J=7.5 Hz, 1H), 7.44-7.57 (m, 5H), 7.60-7.79 (m, 10H), 7.80-7.87 m, 5H), 8.73-8.84 (m, 3H) ppm;

$^{13}$C-NMR (75.5 MHz, $CD_2Cl_2$) δ=121.4, 122.9, 123.5, 123.6, 124.5, 125.4, 126.0, 126.8, 127.3, 127.6, 127.7, 127.9, 128.4, 128.5, 128.6, 128.7, 129.3, 129.5, 129.6, 130.3, 130.4, 130.8, 130.9, 131.7, 132.8, 136.9, 137.7, 138.1, 139.3, 140.1, 144.7, 150.7, 196.3 ppm.

Evaluation Example 1

The energy levels of various singlet excited states and the energy levels of various triplet excited states of Compounds 1 and 2 were calculated according to quantum chemistry computation based on Density Functional Theory (DFT) by using a Gaussian 09 program. The energy level of the $^{3}$n-π* excited state, the energy level of the $^{1}$π-π* excited state, and the energy level of the $^{3}$π-π*excited state were determined. The results of the calculations are shown in Table 1. Compound A1 does not have a $^{3}$n-π* excited state, thus, the data of Compound A1 is not shown in Table 1.

The geometry optimization and single point calculation of a model structure were performed by using a long range corrected version of B3LYP using a Coulomb-attenuating method (CAM-B3LYP) and a 6-311+G(d,p) basis set. The polarizable continuum model (CPCM) parameterized for THF was applied in the geometry optimization. To evaluate convergence stability, frequency calculation was performed. The same functional and basis set used in the geometry optimization was used to apply the TD-DFT calculation to the optimized geometry. The CPCM parameterized for THF was applied to explain solvation effects. Twenty singlet states and triplet states were calculated and analyzed.

The non-bonding and π orbitals were determined according to topologies thereof, and oscillator strengths and expansion coefficients were obtained from log files.

TABLE 1

| Compound No. | Energy level of $^3$n-π* excited state (eV) | Energy level of $^1$π-π* excited state (eV) | Energy level of $^3$π-π* excited state (eV) | Absolute value[1] (eV) | Absolute value[2] (eV) |
|---|---|---|---|---|---|
| 1 | 3.52 | 3.44 | 3.46 | 0.08 | 0.06 |
| 2 | 3.41 | 3.37 | 3.37 | 0.04 | 0.04 |

[1]absolute value of difference between energy level of $^3$n-π* excited state and energy level of $^1$π-π* excited state.
[2]absolute value of difference between energy level of $^3$n-π* excited state and energy level of $^3$π-π* excited state

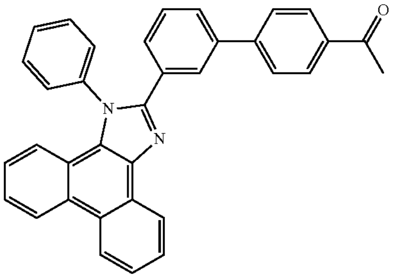

1

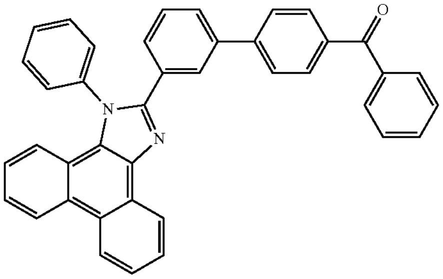

2

Referring to the results of Table 1, Compounds 1 and 2 are each found to have a relatively small absolute value of a difference between the energy level of the $^3$n-π* excited state and the energy level of the $^1$π-π* excited state, and a relatively small absolute value of a difference between the energy level of the $^3$n-π* excited state and the energy level of $^3$π-π* excited state.

In addition, referring to the results of Table 1, Compounds 1 and 2 were each found not to include an additional excited state between the $^3$n-π* excited state and the $^3$π-π* excited state.

Evaluation Example 2

For the optimized triplet structure, the spin-orbit coupling (SOC) value of each of Compounds 1, 2, and A1 were determined by using ZORA calculation method (B3LYO-D3(BJ)/TZ$_2$P) included in AMS2020 program. Then, (1) Rate (rISC), that is, a rate of reverse intersystem crossing of excitons migrating from the $^3$n-π* excited state to the $^1$π-π* excited state, and (2) Rate (IC), that is, a rate of internal conversion of excitons migrating from the $^3$n-π* excited state to the $^3$π-π* excited state of each of Compounds 1, 2, and A1 were calculated by using the energy level difference between excited states (see Equations 1 to 4). The results of the calculations are shown in Table 2.

Rate (rISC) of Compounds 1 and 2 were calculated according to Equation 1, and Rate (IC) of Compounds 1 and 2 were calculated according to Equation 2:

$$\text{Rate }(rISC)=SOC^2/(E(^3n\text{-}\pi^*)-E(^1\pi\text{-}\pi^*))^2 \qquad \text{Equation 1}$$

$$\text{Rate }(IC)=SOC^2/(E(^3n\text{-}\pi^*)-E(^3\pi\text{-}\pi^*))^2 \qquad \text{Equation 2}$$

wherein, in Equations 1 and 2,

SOC represents a spin-orbit coupling value,

E($^3$n-π*) represents an energy level of the $^3$n-π* excited state,

E($^1$π-π*) represents an energy level of the $^1$π-π* excited state, and

E($^3$π-π*) represents an energy level of the $^3$π-π* excited state.

As Compound A1 does not include a $^3$n-π* excited state, Rate (rISC) of Compound A1 was calculated according to Equation 3, and Rate (IC) of Compound A1 was calculated according to Equation 4:

$$\text{Rate }(rISC)=SOC^2/(E(^3\pi\text{-}\pi^*)-E(^1\pi\text{-}\pi)^2 \qquad \text{Equation 3}$$

$$\text{Rate }(IC)\fallingdotseq SOC^2/(E(^3\pi\text{-}\pi^*)-E(^3\pi\text{-}\pi)^2 \qquad \text{Equaion 4}$$

SOC in Equations 3 and 4 represents a spin-orbit coupling value,

E($^1$π-7*) and E($^3$π-π*) in Equations 3 and 4, respectively, represents the energy level of the $^1$π-π* excited state and the energy level of the $^3$π-π* excited state (a set of having the greatest SOC value from among sets of E($^1$π-7*) and E($^3$π-π*) of the Compounds was selected), and E($^3$π-π'*) in Equation 4 is the energy level right under the energy level of the $^3$π-π* excited state.

TABLE 2

| Compound No. | Rate (rISC) (au) | Rate (IC) (au) | Ratio of Rate (rISC) to Rate (IC) (Rate (rISC)/Rate (IC)) |
|---|---|---|---|
| 1 | $3.3 \times 10^{-7}$ | $2.5 \times 10^{-7}$ | 1.3 |
| 2 | $8.6 \times 10^{-8}$ | $8.6 \times 10^{-8}$ | 1.0 |
| A1 | $2.1 \times 10^{-9}$ | $9.1 \times 10^{-9}$ | 0.23 |

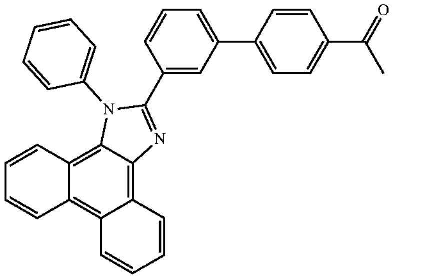

1

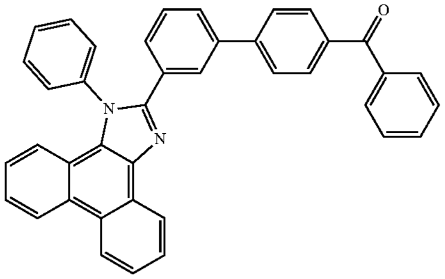

2

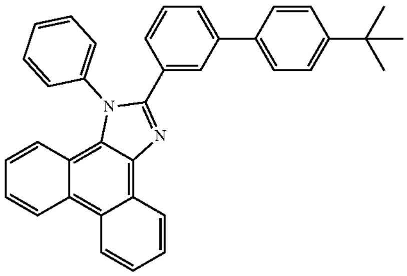

A1

Referring to the results of Table 2, Compounds 1 and 2 were each found to have a relatively large ratio of Rate (rISC) to Rate (IC), as compared with Compound A1.

Evaluation Example 3

A quartz substrate was prepared by washing with acetone isopropyl alcohol and pure water. The materials listed in Table 3 were then vacuum (co)-deposited under a vacuum degree ($10^{-7}$ torr) to prepare Films 1, 2, and A1 each having a thickness of 50 nanometers (nm).

The PL spectrum of each of Films 1, 2, and A1 was evaluated at room temperature by using a time-resolved photoluminescence (TRPL) measurement system, FluoTime 300 (available from PicoQuant), and a pumping source, PLS340 (available from PicoQuant, excitation wavelength=340 nm, spectral width=20 nm). The wavelength of the main peak in the PL spectrum was determined, and upon photon pulses (pulse width=500 picoseconds, ps) applied to the film by PLS340, the number of photons emitted at the wavelength of the main peak for each film was repeatedly measured over time by time-correlated single photon counting (TCSPC) with the TRPL curves available for the sufficient fitting. From the TRPL curves, the decay time of each of Films 1, 2, and A1 was obtained by fitting two or more exponential decay functions. The decay times of each film are shown in Table 3. The functions used for the fitting are as described in Mathematical Equation 10, and a decay time having the largest value among values for each of the exponential decay functions used for the fitting was taken as a decay time. The measurements of decay time were also obtained in a dark state (i.e., a state where a pumping signal incident on each of the films was blocked) while the pulse measurements for obtaining TRPL curves were obtained, thereby obtaining a baseline or a background signal curve available as a baseline for the fitting.

In the case of Films 1, 2, and A1, a curve of prompt fluorescence components and a curve of delayed fluorescence components were used to calculate a decay time.

$$f(t) = \sum_{i=1}^{n} A_i \exp(-t/T_{decay,i})$$ Mathematical Equation 10

TABLE 3

| Film No. | Film Compounds | Decay time (exciton lifetime) |
|---|---|---|
| 1 | Compound 1 and mCBP (volumetric ratio of 15:85) | 0.002134 |
| 2 | Compound 2 and mCBP (volumetric ratio of 15:85) | 0.002345 |
| A1 | Compound A1 and mCBP (volumetric ratio of 15:85) | 0.0086 |

Referring to the results of Table 3, Compounds 1 and 2 were each found to have a relatively small decay time, as compared with Compound A1.

Manufacture of OLED 1

To prepare an anode, a glass substrate, on which an ITO electrode was formed, was cut to a size of 50 millimeters (mm)×50 mm×0.5 mm. Then the glass substrate was sonicated in acetone isopropyl alcohol and pure water for about 15 minutes, and cleaned by exposure to ultraviolet rays with ozone for 30 minutes.

Compounds HT3 and HT-D2 (in which a concentration of Compound HT-D2 was 3 percent by weight (wt %)) were co-deposited on the anode to form a hole injection layer having a thickness of 100 Å. Compound HT3 was deposited on the hole injection layer to form a hole transport layer having a thickness of 1,500 Å. mCP was deposited on the hole transport layer to form an electron blocking layer having a thickness of 100 Å, thereby forming a hole transport region having a thickness of 1,700 Å.

Compound mCBP(as a host) and Compound 1 (as a dopant) were next co-deposited at a volumetric ratio of 85:15 on the hole transport region to form an emission layer having a thickness of 400 Å.

Compound BCP was vacuum-deposited on the emission layer to form a hole blocking layer having a thickness of 100 Å. Compound ET17 and LiQ were co-deposited on the hole blocking layer at a weight ratio of 5:5 to form an electron transport layer having a thickness of 360 Å. LiQ was deposited on the electron transport layer to form an electron injection layer having a thickness of 5 Å. Aluminum (Al) was deposited on the electron injection layer to form a layer of aluminum having a thickness of 120 Å, thereby completing the manufacture of an organic light-emitting device.

HT3

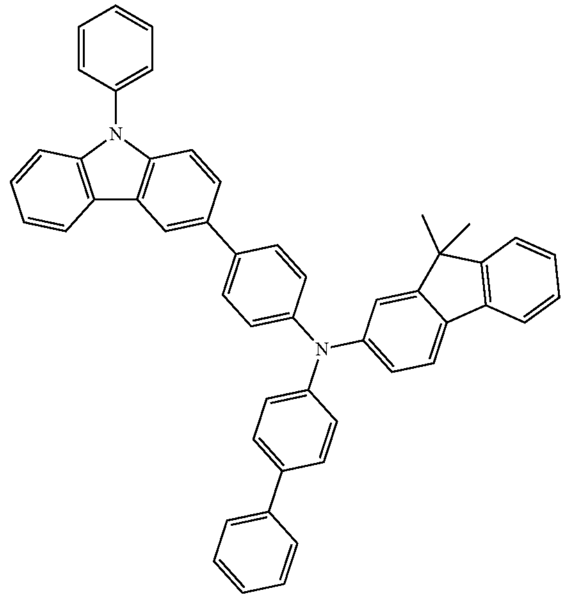

HT-D2

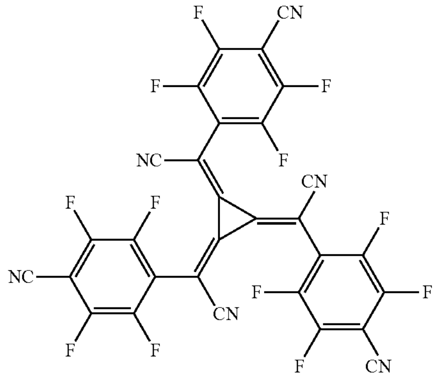

mCP

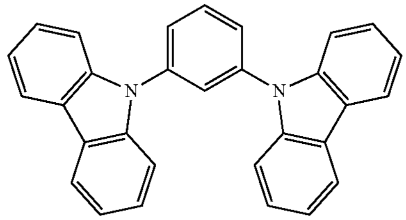

mCBP

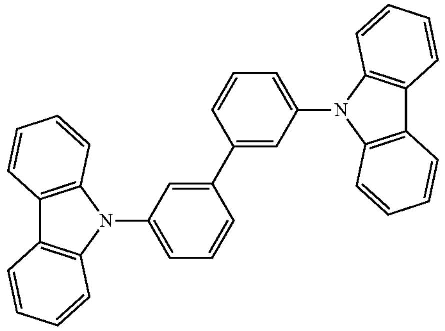

-continued

BCP

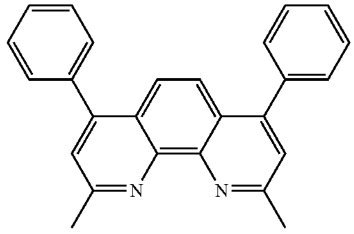

ET17

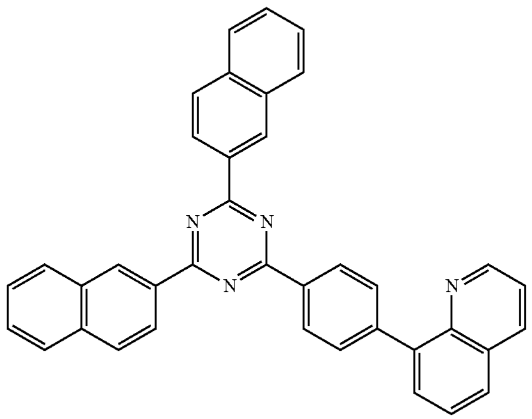

Manufacture of OLED 2 and OLED A1

Organic light-emitting devices were each manufactured in the same manner as in Manufacture of OLED1, except that dopants shown in Table 4 were used in the formation of the emission layer.

Evaluation Example 4

The luminance, photoluminescent quantum yield (PLQY), internal quantum efficiency (IQE), and IQE/PLQY of OLEDs 1, 2, and A1 were measured using Keithley 2400 current voltmeter and a luminance meter (Minolta Cs-1000A). The results are shown in Table 4. IQE/PLQY is a numerical value calculated under the premise that outcoupling efficiency of the devices is assumed to be 0.2264.

TABLE 4

| OLED No. | Dopant Compound No. | Luminance ($cd/m^2$) | PLQY (%) | IQE (%) | IQE/PLQY (%) |
|---|---|---|---|---|---|
| 1 | 1 | 100 | 6.3 | 2.4 | 38.7 |
| 2 | 2 | 100 | 1.9 | 0.8 | 39.5 |
| A1 | A1 | 100 | 52.4 | 8.4 | 15.9 |

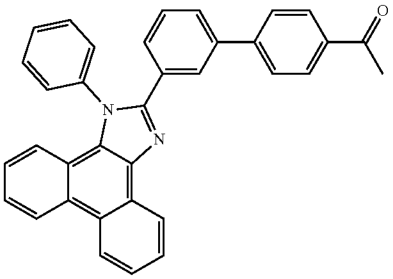

1

TABLE 4-continued

| OLED No. | Dopant Compound No. | Luminance (cd/m$^2$) | PLQY (%) | IQE (%) | IQE/PLQY (%) |
|---|---|---|---|---|---|

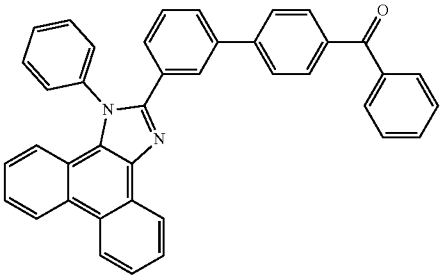

2

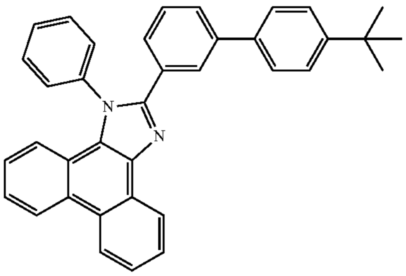

A1

Referring to the results of Table 4, OLEDs 1 and 2 exhibit improved IQE/PLQY characteristics as compared with OLED A1. Accordingly, light emission from Compounds 1 and 2 are observed to be more effective than light emission of Compound A1. We believe this is in-part due to an emission mechanism that allows excitons to migrate from a $^3$n-π* excited state to a $^1$π-π* excited state in the fluorescent compound by intersystem crossing followed by radiative transition to a ground state to emit light via fluorescence.

Many if not most of excitons of the $^3$n-π* excited state may migrate to the $^1$π-π* excited state in the fluorescent compound and then undergo radiative transition to the ground state. It is this migration from triplet to singlet excited states in the fluorescent compound that is likely to provide the observed increase in luminescence efficiency. In addition, the mechanism may provide the fluorescent compound with a shorter exciton lifetime, i.e., a short decay time, which is likely to provide greater device stability or lifetimes. As apparent from the foregoing description, the fluorescent compound may not contain an expensive transition metal such as iridium or platinum, and yet, provide relatively high luminescence efficiency and greater lifespan. Therefore, when the fluorescent compound is used, a light-emitting device having high luminescence efficiency and greater lifespan may be manufactured at a low cost compared phosphorescent emitter complexes.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A light-emitting device comprising:

a first electrode; a second electrode facing the first electrode; and an organic layer disposed between the first electrode and the second electrode, the organic layer comprising an emission layer and a fluorescent compound, wherein, upon excitation, excitons in a $^3$n-π* excited state of the fluorescent compound migrate to a $^1$π-π* excited state of the fluorescent compound by reverse intersystem crossing with a Rate (rISC), and the excitons in the $^1$π-π* excited state undergo radiative transition to a ground state to emit light via fluorescence, and excitons in the $^3$n-π* excited state of the fluorescent compound migrate to a $^3$π-π* excited state of the fluorescent compound through reverse internal conversion with a Rate (IC), wherein a ratio of Rate (rISC) to Rate (IC) is 0.5 or greater, the index "$^3$" in "$^3$n-π*" and "$^3$π-π*" represents a triplet state, and the index"$^1$" in "$^1$π-π*" represents a singlet state, Rate (rISC) is evaluated by Equation 1, and Rate (IC) is evaluated by Equation 2:

$$\text{Rate } (rISC)=SOC^2/(E(^3n\text{-}\pi^*)-E(^1\pi\text{-}\pi^*))^2 \quad \text{Equation 1}$$

$$\text{Rate } (IC)=SOC^2/(E(^3n\text{-}\pi^*)-E(^3\pi\text{-}\pi^*))^2 \quad \text{Equation 2}$$

wherein, in Equations 1 and 2,

SOC represents a spin-orbit coupling value,

E($^3$n-π*) represents an energy level of the $^3$n-π* excited state,

E($^1$π-π*) represents an energy level of the $^1$π-π* excited state,

E(π-π*) represents an energy level of the $^3$π-π* excited state, and

SOC, E($^3$π-π*), E($^1$π-π*), and E($^3$π-π*) are each evaluated according to density functional theory, wherein an absolute value of a difference between an energy level of the $^3$n-π* excited state in the fluorescent compound and an energy level of the $^3$π-π* excited state in the fluorescent compound is in a range of about 0 electron volts to about 0.1 electron volts.

2. The light-emitting device of claim 1, wherein the ratio of Rate (rISC) to Rate (IC) is in a range of about 0.8 to about 1.5.

3. The light-emitting device of claim 1, wherein the ratio of Rate (rISC) to Rate (IC) is in a range of about 1.0 to about 1.3.

4. The light-emitting device of claim 1, wherein an energy level of the $^3$n-π* excited state is greater than the lowest energy level among energy levels of the $^1$π-π* excited state in the fluorescent compound.

5. The light-emitting device of claim 1, wherein an absolute value of a difference between an energy level of the $^3$n-π* excited state in the fluorescent compound and the lowest energy level among energy levels of the $^1$π-π* excited state in the fluorescent compound is in a range of about 0 electron volts to about 0.15 electron volts.

6. The light-emitting device of claim 1, wherein an energy level of the $^3$π-π* excited state is greater than an energy level of the $^3$π-π* excited state in the fluorescent compound.

7. The light-emitting device of claim 1, wherein an additional excited state is not present between the $^3$n-π* excited state and the $^3$π-π* excited state in the fluorescent compound.

8. The light-emitting device of claim 1, wherein the fluorescent compound has a non-bonding orbital.

9. The light-emitting device of claim 1, wherein the fluorescent compound has at least one carbonyl group.

10. The light-emitting device of claim 1, wherein the fluorescent compound is represented by Formula 1-1:

Formula 1-1

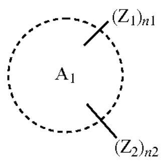

Formula 2-1

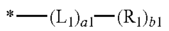

Formula 2-2

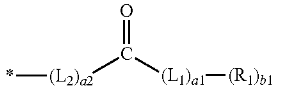

wherein, in Formula 1-1, ring $A_1$ is a $C_5$-$C_{60}$ carbocyclic group or a $C_1$-$C_{60}$ heterocyclic group, $Z_1$ in Formula 1-1 is a group represented by Formula 2-1 or a group represented by Formula 2-2, and n1 is an integer from 0 to 20, $Z_2$ in Formula 1-1 is a group represented by Formula 2-2, and n2 is an integer from 1 to 40, $L_1$ and $L_2$ in Formulae 2-1 and 2-2 are each independently a single bond, a $C_5$-$C_{60}$ carbocyclic group unsubstituted or substituted with at least one $R_{10a}$, or a $C_1$-$C_{60}$ heterocyclic group unsubstituted or substituted with at least one $R_{10a}$, a1 and a2 in Formulae 2-1 and 2-2 are each independently an integer from 1 to 20, wherein $R_1$ and each $R_{10a}$ in Formulae 2-1 and 2-2, are each independently hydrogen, deuterium, —F, —Cl, —Br, —I, —$SF_5$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$, —$B(Q_6)(Q_7)$, or —$P(=O)(Q_8)(Q_9)$, b1 in Formulae 2-1 and 2-2 is an integer from 1 to 20,

* in Formulae 2-1 and 2-2 indicates a binding site to an adjacent atom, and at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is:

deuterium, —F, —Cl, —Br, —I, -$CD_3$, -$CD_2H$, -$CDH_2$, —$CF_3$, —$CF_2H$, —$CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with deuterium, —F, —Cl, —Br, —I, -$CD_3$, -$CD_2H$, -$CDH_2$, —$CF_3$, —$CF_2H$, —$CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, —$B(Q_{16})(Q_{17})$, —$P(=O)(Q_{18})(Q_{19})$, or any combination thereof;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group, each unsubstituted or substituted with deuterium, —F, —Cl, —Br, —I, -$CD_3$, -$CD_2H$, -$CDH_2$, —$CF_3$, —$CF_2H$, —$CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, —$B(Q_{26})(Q_{27})$, —$P(=O)(Q_{28})(Q_{29})$, or any combination thereof; or —$N(Q_{31})(Q_{32})$, —$Si(Q_{33})(Q_{34})(Q_{35})$, —$B(Q_{36})(Q_{37})$, or —$P(=O)(Q_{38})(Q_{39})$, wherein $Q_1$ to $Q_9$, $Q_{11}$ to $Q_{19}$, $Q_{21}$ to $Q_{29}$, and $Q_{31}$ to $Q_{39}$ are each independently hydrogen, deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one selected from deuterium, a $C_1$-$C_{60}$ alkyl group, and a $C_6$-$C_{60}$ aryl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one selected from deuterium, a $C_1$-$C_{60}$ alkyl group, and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group.

11. The light-emitting device of claim 10, wherein ring $A_1$ in Formula 1-1 is a nitrogen-containing $C_1$-$C_{60}$ heteropolycyclic group.

12. The light-emitting device of claim 10, wherein ring $A_1$ in Formula 1-1 is a group represented by one of Formulae A1-1 to A1-6:

A1-1

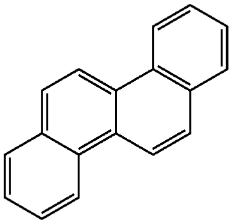

A1-2

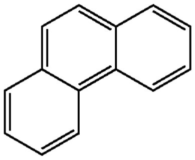

A1-3

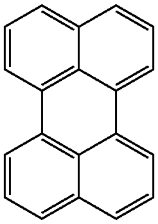

A1-4

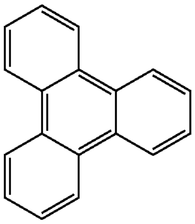

A1-6

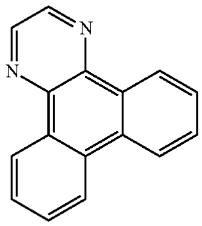

wherein, in Formula A1-5, $X_1$ is O, S, $N(Z_1)$, $N(Z_2)$, or $C(Z_{11})(Z_{12})$, wherein $Z_{11}$ and $Z_{12}$ are independently a group defined by $Z_1$.

13. The light-emitting device of claim 10, wherein n2 in Formula 1-1 is 1 or 2.

14. The light-emitting device of claim 10, wherein the fluorescent compound is represented by Formula A (1) or Formula A(2):

A(1)

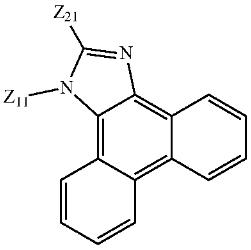

A(2)

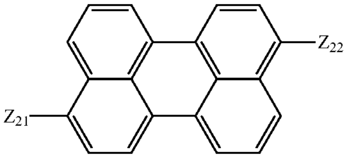

wherein, in Formulae A(1) and A(2), wherein $Z_{11}$ and $Z_{12}$ are independently a group defined by $Z_1$, and $Z_{21}$ and $Z_{22}$ are independently a group defined by $Z_2$.

15. The light-emitting device of claim 1, wherein the fluorescent compound is one of Compounds 1, 2, 3, or 4

1

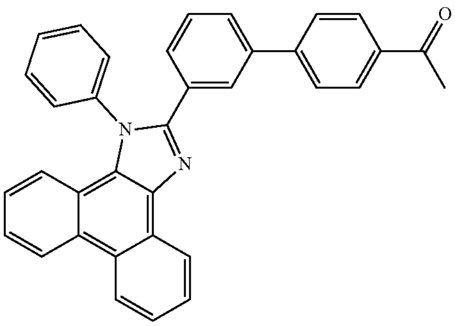

2

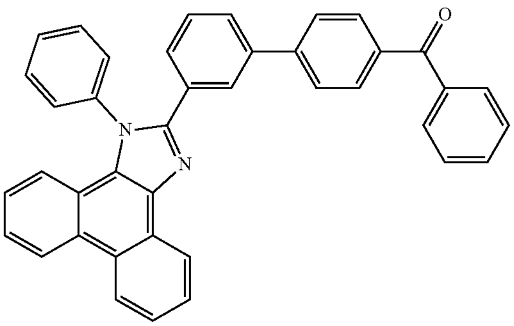

3

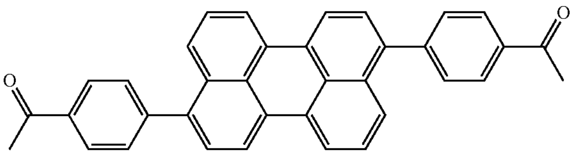

-continued

4

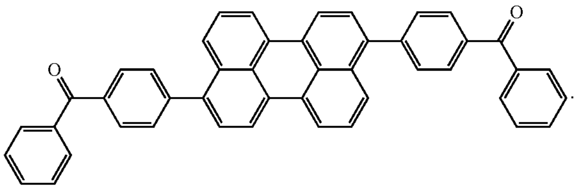

16. A light-emitting device comprising:

a first electrode; a second electrode facing the first electrode; and an organic layer disposed between the first electrode and the second electrode, the organic layer comprising an emission layer and a fluorescent compound, wherein, upon excitation, excitons in a $^3$n-π* excited state of the fluorescent compound migrate to a $^1$π-π* excited state of the fluorescent compound by reverse intersystem crossing with a Rate (rISC), and the excitons in the $^1$π-π* excited state undergo radiative transition to a ground state to emit light via fluorescence, and excitons in the $^3$n-π* excited state of the fluorescent compound migrate to a $^3$π-π* excited state of the fluorescent compound through reverse internal conversion with a Rate (IC), wherein a ratio of Rate (rISC) to Rate (IC) is 0.5 to 1.5, the index "$^3$" in "$^3$n-π*" and "$^3$π-π*" represents a triplet state, and the index "$^1$" in "$^1$π-π*" represents a singlet state, Rate (rISC) is evaluated by Equation 1, and Rate (IC) is evaluated by Equation 2:

$$\text{Rate }(rISC)=SOC^2/(E(^3n\text{-}\pi^*)-E(^1\pi\text{-}\pi^*))^2 \quad \text{Equation 1}$$

$$\text{Rate }(IC)=SOC^2/(E(^3n\text{-}\pi^*)-E(^3\pi\text{-}\pi^*))^2 \quad \text{Equation 2}$$

wherein, in Equations 1 and 2,

SOC represents a spin-orbit coupling value,

E($^3$n-π*) represents an energy level of the $^3$n-π* excited state,

E($^1$π-π*) represents an energy level of the $^1$π-π* excited state,

E($^3$π-π*) represents an energy level of the $^3$π-π* excited state, and

SOC, E($^3$n-π*), E($^1$π-π*), and E(3π-π*) are each evaluated according to density functional theory, wherein the fluorescent compound is represented by Formula 1-1:

Formula 1-1

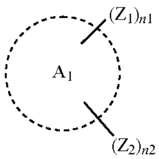

Formula 2-1

$$*—(L_1)_{a1}—(R_1)_{b1}$$

Formula 2-2

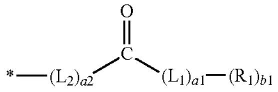

wherein, in Formula 1-1, ring $A_1$ is a $C_5$-$C_{60}$ carbocyclic group or a $C_1$-$C_{60}$ heterocyclic group, $Z_1$ in Formula 1-1 is a group represented by Formula 2-1 or a group represented by Formula 2-2, and n1 is an integer from 0 to 20, $Z_2$ in Formula 1-1 is a group represented by Formula 2-2, and n2 is an integer from 1 to 40, Land $L_2$ in Formulae 2-1 and 2-2 are each independently a single bond, a $C_5$-$C_{60}$ carbocyclic group unsubstituted or substituted with at least one $R_{10a}$, or a $C_1$-$C_{60}$ heterocyclic group unsubstituted or substituted with at least one $R_{10a}$, a1 and a2 in Formulae 2-1 and 2-2 are each independently an integer from 1 to 20, and ring $A_1$ in Formula 1-1 is a group represented by one of Formulae A1-1 to A1-4 and A1-6:

A1-1

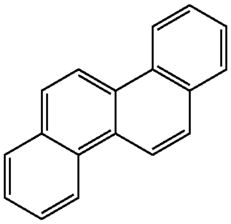

A1-2

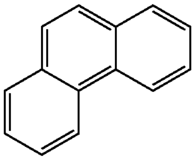

A1-3

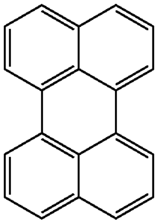

A1-4

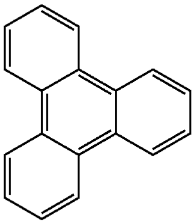

A1-6

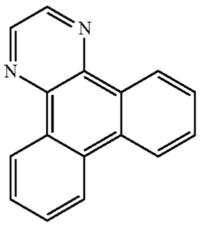

wherein $R_1$ and each $R_{10a}$ in Formulae 2-1 and 2-2, are each independently hydrogen, deuterium, —F, —Cl, —Br, —I, —$SF_5$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), —B($Q_6$)($Q_7$), or —P(=O)($Q_8$)($Q_9$), b1 in Formulae 2-1 and 2-2 is an integer from 1 to 20,

* in Formulae 2-1 and 2-2 indicates a binding site to an adjacent atom.

17. A light-emitting device comprising:

a first electrode; a second electrode facing the first electrode; and an organic layer disposed between the first electrode and the second electrode, the organic layer comprising an emission layer and a fluorescent compound, wherein, upon excitation, excitons in a $^3$n-π* excited state of the fluorescent compound migrate to a $^1$π-π* excited state of the fluorescent compound by reverse intersystem crossing with a Rate (rISC), and the excitons in the $^1$π-π* excited state undergo radiative transition to a ground state to emit light via fluorescence, and excitons in the $^3$n-π* excited state of the fluorescent compound migrate to a $^3$π-π* excited state of the fluorescent compound through reverse internal conversion with a Rate (IC), wherein a ratio of Rate (rISC) to Rate (IC) is 0.5 to 1.5, the "$^3$" in "$^3$n-π*" and "$^3$π-π*" represents a triplet state, and the "$^1$" in "$^1$π-π*" represents a singlet state, Rate (rISC) is evaluated by Equation 1, and Rate (IC) is evaluated by Equation 2:

$$\text{Rate }(rISC)=SOC^2/(E(^3n\text{-}\pi^*)-E(^1\pi\text{-}\pi^*))^2 \quad \text{Equation 1}$$

$$\text{Rate }(IC)=SOC^2/(E(^3n\text{-}\pi^*)-E(^3\pi\text{-}\pi^*))^2 \quad \text{Equation 2}$$

wherein, in Equations 1 and 2,

SOC represents a spin-orbit coupling value,

E($^3$n-π*) represents an energy level of the $^3$n-π* excited state,

E($^1$π-π*) represents an energy level of the $^1$π-π* excited state,

E($^3$π-π*) represents an energy level of the $^3$π-π* excited state, and

SOC, E($^3$n-π*), E($^1$π-π*), and E($^3$π-π*) are each evaluated according to density functional theory, wherein an absolute value of a difference between an energy level of the $^3$n-π* excited state in the fluorescent compound and the lowest energy level among energy levels of the $^1$π-π* excited state in the fluorescent compound is in a range of about 0 electron volts to about 0.15 electron volts.

18. The light-emitting device of claim 16, wherein at least two of the following conditions are satisfied:

an additional excited state is not present between the $^3$n-π* excited state and the $^3$π-π* excited state in the fluorescent compound;

the fluorescent compound has a non-bonding orbital; and the fluorescent compound has at least one carbonyl group.

19. The light-emitting device of claim 17, wherein at least two of the following conditions are satisfied:

an additional excited state is not present between the $^3$n-π* excited state and the $^3$π-π* excited state in the fluorescent compound;

the fluorescent compound has a non-bonding orbital; and the fluorescent compound has at least one carbonyl group.

* * * * *